(12) United States Patent
Bao et al.

(10) Patent No.: US 8,808,382 B2
(45) Date of Patent: Aug. 19, 2014

(54) IMPLANT RETENTION DEVICE AND METHOD

(75) Inventors: Qi-Bin Bao, Marquette, MI (US); Jeffrey L. Trudeau, Marquette, MI (US); Thomas S. Kilpela, Marquette, MI (US); Wade DePas, Ishpeming, MI (US); Allison Koskey, Ishpeming, MI (US); Brian P. Janowski, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 70 days.

(21) Appl. No.: 11/963,727

(22) Filed: Dec. 21, 2007

(65) Prior Publication Data

US 2008/0167721 A1      Jul. 10, 2008

Related U.S. Application Data

(60) Provisional application No. 60/948,273, filed on Jul. 6, 2007, provisional application No. 60/871,641, filed on Dec. 22, 2006.

(51) Int. Cl.
   *A61F 2/44* (2006.01)
(52) U.S. Cl.
   USPC ..................... 623/17.14; 623/17.15
(58) Field of Classification Search
   USPC ........................... 623/17.11–17.16
   See application file for complete search history.

(56) References Cited

U.S. PATENT DOCUMENTS

| | | | |
|---|---|---|---|
| 5,269,809 A * | 12/1993 | Hayhurst et al. | 606/232 |
| 6,648,903 B1 | 11/2003 | Pierson, III | |
| 6,733,531 B1 * | 5/2004 | Trieu | 623/17.11 |
| 6,974,479 B2 | 12/2005 | Trieu | |
| 7,338,525 B2 * | 3/2008 | Ferree | 623/17.11 |
| 2002/0151979 A1 * | 10/2002 | Lambrecht et al. | 623/17.16 |
| 2003/0078579 A1 * | 4/2003 | Ferree | 606/53 |
| 2003/0195514 A1 * | 10/2003 | Trieu et al. | 606/61 |
| 2003/0204260 A1 * | 10/2003 | Ferree | 623/17.11 |
| 2004/0002764 A1 * | 1/2004 | Gainor et al. | 623/17.16 |
| 2004/0030392 A1 * | 2/2004 | Lambrecht et al. | 623/17.16 |

(Continued)

FOREIGN PATENT DOCUMENTS

| | | |
|---|---|---|
| WO | 0195818 | 12/2001 |
| WO | 2005092208 | 10/2005 |

OTHER PUBLICATIONS

International Search Report, International Searching Authority, Form PCT/ISA/210 for Corresponding International Application No. PCT/US2007/088739 dated May 22, 2008 (2 pages).

(Continued)

*Primary Examiner* — Pedro Philogene
*Assistant Examiner* — Lynnsy Schneider
(74) *Attorney, Agent, or Firm* — Fitch, Even, Tabin & Flannery LLP

(57) ABSTRACT

An implant retention device is provided to assist in restraining movement of a nuclear implant and to assist in preventing expulsion of the nuclear implant through an incision portal or defect in the annular wall. In one form, the implant retention device may include an elongated tensioning member having a portion configured to connect to the implant and at least one anchoring device disposed on the tensioning member, the anchoring device configured to at least partially penetrate spinal tissue such as the annulus, vertebral body, or other secure tissue.

18 Claims, 20 Drawing Sheets

(56) References Cited

U.S. PATENT DOCUMENTS

| | | |
|---|---|---|
| 2004/0186573 A1 | 9/2004 | Ferree |
| 2004/0210226 A1* | 10/2004 | Trieu ............................. 606/72 |
| 2005/0015150 A1 | 1/2005 | Lee |
| 2005/0125066 A1 | 6/2005 | McAfee |
| 2005/0143826 A1* | 6/2005 | Zucherman et al. ....... 623/17.16 |
| 2005/0216087 A1* | 9/2005 | Zucherman et al. ....... 623/17.16 |
| 2006/0004454 A1 | 1/2006 | Ferree et al. |
| 2006/0089646 A1 | 4/2006 | Bonutti |
| 2006/0217812 A1 | 9/2006 | Lambrecht et al. |
| 2006/0229623 A1 | 10/2006 | Bonutti et al. |
| 2006/0247665 A1* | 11/2006 | Ferree ........................... 606/151 |
| 2006/0247776 A1 | 11/2006 | Kim |
| 2006/0253132 A1* | 11/2006 | Evans et al. .................... 606/151 |
| 2007/0118226 A1* | 5/2007 | Lambrecht et al. ......... 623/17.16 |

OTHER PUBLICATIONS

Supplementary European Search Report issued in the counterpart European Application No. EP 07 855 339.3 dated Nov. 23, 2013 (6 pages).

* cited by examiner

IMPLANT RETENTION DEVICE AND METHOD

CROSS REFERENCE TO RELATED APPLICATIONS

This application claims the benefit of U.S. Provisional Application No. 60/871,641, filed Dec. 22, 2006, and U.S. Provisional Application No. 60/948,273, filed Jul. 6, 2007, both of which are hereby incorporated by reference as if reproduced herein in their entirety.

FIELD OF THE INVENTION

The invention relates to artificial intervertebral implants and devices for securing and retaining the implant in an intervertebral space.

BACKGROUND OF THE INVENTION

The most common orthopedic condition for which professional medical treatment is sought is lower back pain. Although many factors may be responsible for causing lower back pain, a principal factor is damage or degeneration of an intervertebral spinal disc resulting in impingement on the nerve system, specifically the spinal cord, located within the spine. Such impingement may result in, for instance, loss of mobility, urinary and fecal incontinence, and sciatica or pain experienced in the extremities.

Damage to or degeneration of a spinal disc can result from a number of factors such as abuse or age. The disc itself is composed primarily of an annulus and a nucleus contained therein. The annulus is a fibrous annular piece that attaches to the adjacent vertebrae and contains the nucleus, which is in turn a gel-like viscous material capable of shock absorption and flowable to permit poly-axial rotation and resilient compression of the vertebrae and spine. Most frequently, disc degeneration results from damage occurring to the annulus such that the flowable nucleus material may leak or seep out of the annulus. Disc degeneration also can occur in other ways, such as by being deprived of nutrient flow leading to a dried and susceptible to damage disc. Because the nuclear material is flowable, extensive damage to the annulus is not necessary for leakage to occur.

A recent, though not new, development for spinal surgery is a procedure known as disc arthroplasty for restoring or reconstructing the disc using a prosthesis to replace a portion or entirety of the damaged disc. The primary objective of disc arthroplasty is to restore or maintain the normal disc anatomy and functions, while addressing and treating the causes of the pain.

Two types of prostheses for disc arthroplasty are currently believed to merit further development by medical science and research. One type is a total disc prosthesis, or TDP, where the entire spinal disc is replaced after radial discectomy. A typical TDP includes structures that together mimic the properties of a natural disc.

The other type is a disc nucleus prosthesis, or DNP, that is used to replace only the nucleus of a spinal disc after a nucleotomy while retaining the annulus of the disc and, possibly, the end plates intact. As discussed above, failure of the natural disc does not require extensive damage to the annulus, and the annulus would often be capable of retaining a non-flowing prosthetic nucleus. Implantation of a DNP involves clearing of the natural nucleus from the annulus through the procedure known as nucleotomy, and inserting the DNP within the annulus. Accordingly, disc nuclear prostheses (DNPs) are typically smaller and require less extensive surgery than TDPs do.

An issue related to DNPs is implant extrusion, defined as the tendencies for an implant not to remain seated, and for the implant to back out of its intended seat in the nuclear space. To prevent this, many designs for disc implants attempt to secure to the end plates of the vertebrae by providing securement features on the implant. The nuclear implants frequently have one or more restraining features, such as, for example, keels or other implant protrusions that seat into the bone, apertures integrated into the implant for bone in-growth such as a porous surface or coatings, or screws to screw the implant to the bone. These and other similar features restrain the implant in a predetermined orientation to the surrounding boney bodies to thereby properly support the skeletal structure and prevent damage of any soft tissues. These features, however, may violate the integrity of the end plates to a degree where revision surgery is limited. Violation of the vertebrae by the securement may cause bleeding, or calcification of the end plate, either of which can result in pain, loss of mobility, necrosis, or deterioration of any implant device.

Some arthroplasty devices are designed to float or sit unrestrained within a ligamentous joint capsule. These devices may rely purely on the soft tissue holding the replacement device in the predetermined position. An unrestrained intervertebral artificial nucleus device would benefit from an intact annulus to secure the implant in the predetermined position and prevent its expulsion into the sensitive nerve structure located just outside the annulus. The health of the annulus, however, is often compromised through the degenerative disc disease process and may not be intact. The annulus may have tears or may be poorly nourished and weak such that it cannot adequately serve by itself to restrain the nucleus replacement device within the confines of the annulus. Additionally, the annulus is typically incised during surgery to make an opening for removal of the diseased nucleus material and to serve as a window for placing the nucleus replacement device in its predetermined position. It is possible for this window to serve as an undesired expulsion portal for the nucleus implant.

For these and other reasons, the implant retention devices described herein may be utilized to assist in the retention of a nuclear implant, particularly those that do not have other restraining features, in a predetermined skeletal relationship.

SUMMARY OF THE INVENTION

In accordance with an aspect of the present invention, an implant retention device is provided to assist in restraining movement of a nuclear implant and to assist in limiting expulsion of the nuclear implant through an incision portal or defect in the annular wall. By one approach, an implant retention device comprises at least one elongated tensioning member, such as a wire, suture, cable, or rod, having a portion configured to connect to the implant. The elongated tension member may optionally comprise a composite of a pair of tensioning members secured together by a fastener, such as a crimp. By one approach, the tensioning member extends from a leading end of the implant. At least one anchoring device is disposed on the tensioning member. The anchoring device is configured to at least partially penetrate an inner surface of the annular wall to tether the implant the annular wall. The anchoring device may be disposed adjacent one or both terminal ends of the tensioning member or along the length of the tensioning member. The implant may include at least one hole or other feature to accommodate the tensioning member such that the tensioning member can connect to the implant. In one form, the tensioning member may be threaded through a retaining plug in the implant, wherein a hole in the retaining plug is generally aligned with a hole through the implant. A two-part implant may be comprised, for example, of a top and bottom shell, with the tensioning member and the features to accommodate the tensioning member may be associated with either of the shells. A pivot connection between the anchoring device and the tensioning member facilitates engagement of the anchoring device with the annular wall. The pivot connection allows the anchoring device to pivot between a first position wherein a longitudinal axis of the anchoring device is generally parallel to the tensioning member and a second position wherein the longitudinal axis of the anchoring device is generally perpendicular to the tensioning member. The pivot connection may comprise, for example, a hole through the anchoring device with the tensioning member threaded therethrough. Alternatively, for a rod-type tensioning member, the anchoring device may be pivotally disposed between a pair of prong-type features at a terminal end of the rod.

By another approach, a method is provided wherein an implant retention device is provided for insertion through an opening in an annular wall. The implant retention device includes an elongated tensioning member and an anchoring device disposed on the tensioning member, wherein the anchoring device is configured to at least partially penetrate an inner surface of the annular wall. The anchoring device is then engaged with the inner surface of the annular wall, with the tensioning member extending from the engaged anchoring device. The anchoring device may be engaged with the inner surface of the annular wall, for example, by positioning the anchoring device such that a longitudinal axis of the anchoring device is generally parallel to the tensioning member. At least a portion of the anchoring device then penetrates the inner surface of the annular wall. The anchoring device is then oriented such that the longitudinal axis of the anchoring device is generally perpendicular to the tensioning member. The tensioning member is then connected to the nuclear implant, such as, for example, by threading the tensioning member through a hole or other feature in the implant, such that the nuclear implant is anchored by the anchoring device to restrain movement of the implant.

By another approach, a method for inserting a nuclear implant within an intervertebral space includes providing a nuclear implant with a fastening portion for connecting to a securing mechanism. The securing mechanism includes a tensioning member and an anchoring device. The securing mechanism is inserted within the intervertebral space and secured to a spinal tissue, such as the annulus, a vertebral endplate or a vertebral bone. The nuclear implant is guided into the intervertebral space by moving the implant along the tensioning member. The tensioning member generally passes through a guide portion on the implant, such as a channel or throughbore disposed within the implant. The interaction between the guide member and the tensioning member allows the implant to be guided into the nuclear space along the tensioning member. Depending on where the securing mechanism is secured in relation to the annular opening, the tensioning member may cause the longitudinal orientation of the implant to change as the implant is guided along the tensioning member into the intervertebral space. In this way, the implant may be steered into a desired orientation within the intervertebral space simply by moving the implant along the tensioning member. The tensioning member may be tensioned or pulled taut to help guide the implant.

DETAILED DESCRIPTION

Figure 1:
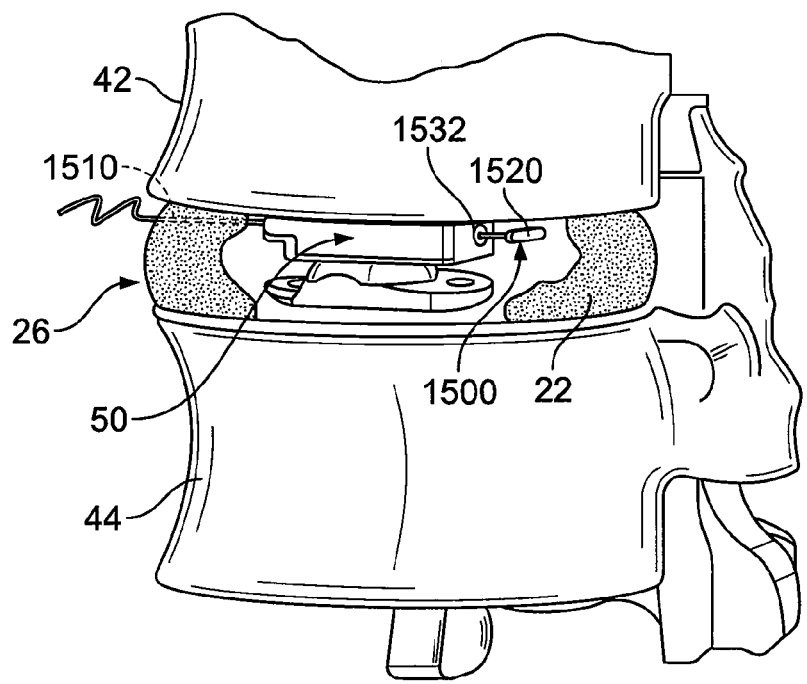
FIG. 1 is a perspective view of a first embodiment of an implant retention device threaded through a nuclear implant and implanted in the annular wall, with the nuclear implant inserted in a nuclear space of a spinal section.
Figure 2:
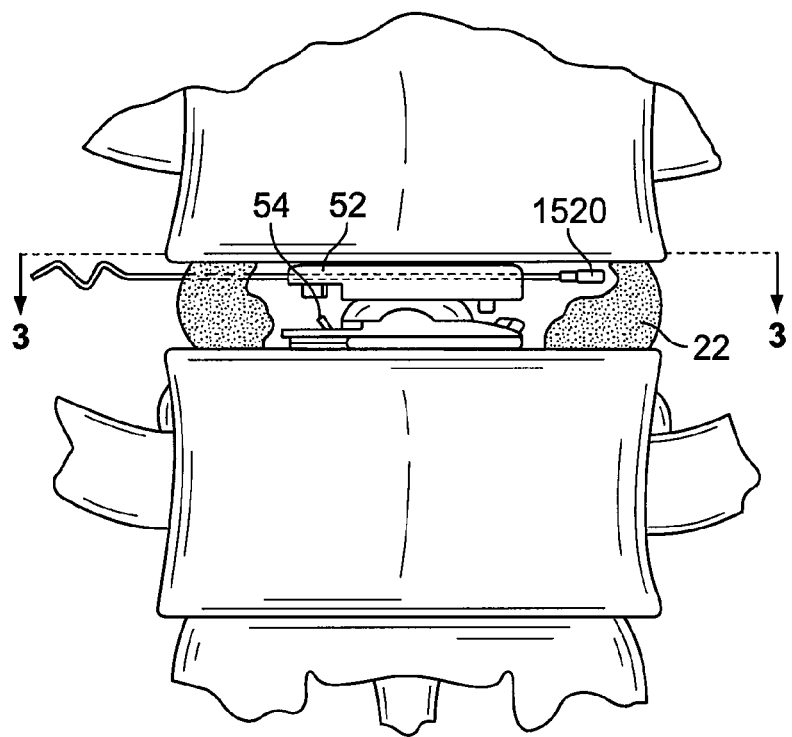
FIG. 2 is a partial front view of the implant retention device, nuclear implant, and spinal section of FIG. 1.
Figure 3:
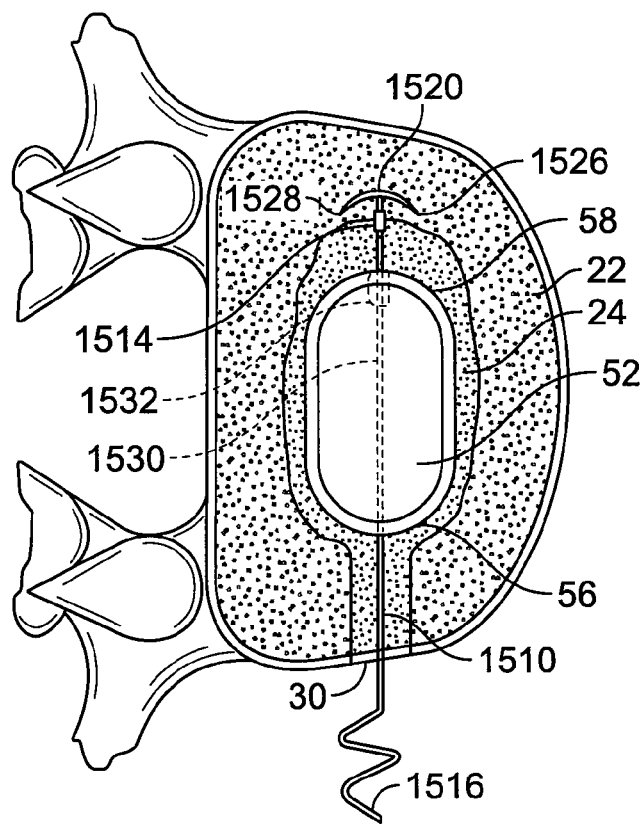
FIG. 3 is a cross-sectional top view of the spinal section of FIG. 2 taken along line 3-3 thereof and showing the nuclear implant with the implant retention device threaded therethrough.
Figure 4:
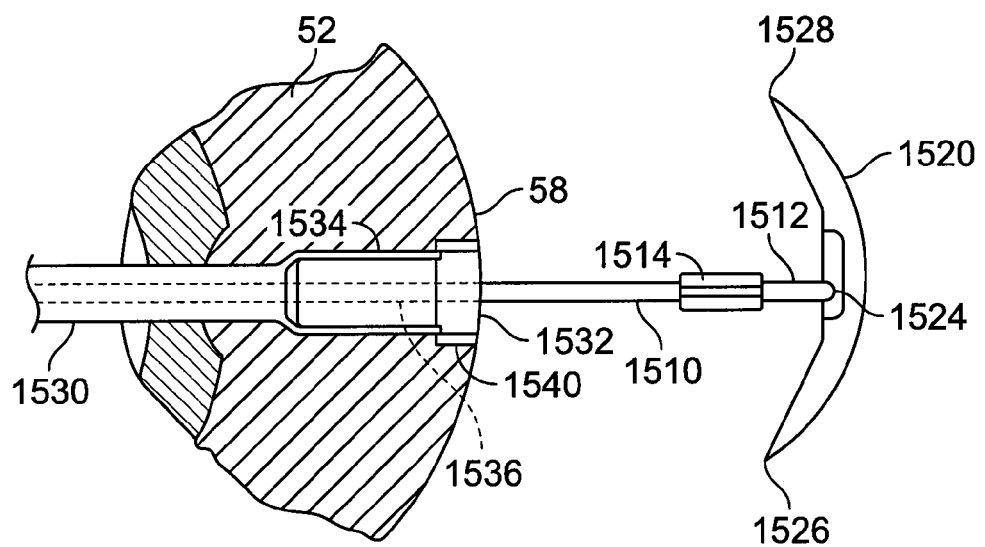
FIG. 4 is a fragmentary cross-sectional top view of the top shell of the nuclear implant of FIG. 3.

Generally speaking, pursuant to these various embodiments, implant retention devices are disclosed herein, with each device directed to maintaining a nuclear implant in position within a nuclear space and limiting the implant from being expelled from or backing out through an opening in the annulus. It shall be understood that retention refers to retaining, restraining, controlling, or maintaining the implant within the nuclear space to limit the expulsion of the implant out of the nuclear space through the annular opening. Referring now to the drawings, and in particular to FIGS. 1-3, a first embodiment of an implant retention device 1500 is shown. A nuclear implant 50 is inserted through an annular opening 30 in the wall of the annulus 22 and positioned within a nuclear space 24 of a disc 26 located between adjacent upper vertebra 42 and lower vertebra 44. The annular opening 30 is typically created during surgery prior to implantation of the nuclear implant 50 to serve as a portal for removing the nucleus and as a surgical window for inserting the implant 50 into the nuclear space 24. However, the annular opening 30 can also be formed from a tear or weakening of the annulus 22. The annular opening 30 generally extends from the exterior of the annulus 22 through to the nuclear space 24. The implant retention device, for this and other implant retention device embodiments disclosed herein, is generally shown being used in conjunction with a nuclear implant 50 comprising a top shell 52 and a bottom shell 54. Each shell 52, 54 has a peripheral shape of an oval or racetrack shape, having a greater longitudinal dimension than a lateral dimension. A concave recess is formed in the top shell 52 and a corresponding dome surface is formed in the bottom shell 54, with the dome surface being received in the concave recess to allow for relative translational motion and movement between the top shell 52 and the bottom shell 54. The nuclear implant 50 shown and described herein is used as an illustrative example, with other configurations of nuclear implants or nuclear replacement devices being contemplated for use in conjunction with the implant retention devices discussed herein.

Referring now to FIGS. 1-4, an implant retention device 1500 is comprised of a tensioning member 1510 and a harpoon 1520 for embedding in the annulus 22 opposite the annular opening 30. The harpoon 1520 has a generally arcuate shape, with at least one sharp end 1526 or 1528 for piercing the annulus 22, although other configurations are contemplated. The harpoon 1520 has a connection portion, such as a hole 1524 therethrough, for pivotally connecting the elongated tensioning member 1510 to the harpoon 1520. The hole 1524 is preferably centrally located on the harpoon 1520. The elongated tensioning member 1510 may be in the form of a cable, wire, or suture that is threaded through the hole 1524. The tensioning member 1510 may be formed from a single length of cable, wire, or suture, or may have a composite construction including an anchor cable connected to the harpoon 1520 and a suture secured to the anchor cable using, for example, a crimp. An end portion 1512 of the tensioning member 1510 is threaded through the hole 1524 and is then preferably mated with the remaining portion of the tensioning member 1510 and secured to the tensioning member 1510 using, for example, at least one crimp 1514.

An instrument, such as forceps, for example, may be used to grasp the harpoon 1520 at one sharp end 1526 and lead the harpoon 1520 through the annular opening 30 to the inner wall of the annulus 22. If both ends 1526, 1528 of the harpoon 1520 have sharp ends, then either end 1526 or 1528 can be used as the leading end. With the end 1526 oriented in the leading position, the longitudinal axis of the harpoon 1520 is generally parallel with the longitudinal axis of the tensioning member 1510. Using 1526 of the harpoon 1520 as the leading end, the leading end 1526 is punctured into the thickness of the annulus 22 from the interior of the nuclear space 24 and pushed through a curved path deep into the annulus 22 such that the entire harpoon 1520 is situated within the annulus. The harpoon 1520 is preferably embedded in the annulus 22 in an area generally opposite the annular opening 30. When the tensioning member 1510 is pulled, the trailing end 1528 of the harpoon 1520 further engages with a portion of the annulus 22 causing the harpoon 1520 to securely position itself such that the longitudinal axis of the harpoon 1520 is generally transverse to the tensioning member 1510 axis. The harpoon 1520 may be pushed completely through the annulus 22 to ultimately rest against the outer annulus wall, or may rest somewhere within the annulus wall 22.

The top shell 52 of the nuclear implant 50 comprises a longitudinal elongated hole 1530 extending between ends 56, 58 of the implant 50 wherein a free end 1516 of the tensioning member 1510 is threaded therethrough to secure the tensioning member 1510 to the implant 50. Once the harpoon 1510 is embedded in the annular wall 22, the tensioning member 1520 is then pulled tight and threaded through the longitudinal hole 1530 of the implant 50. The implant 50 is then inserted into a predetermined position within the nuclear space 24. The free end 1516 of the tensioning member is then tied off, crimped, or otherwise secured such that the implant 50 is then tethered to the annulus 22 and resists moving back through the annular opening 30 and being expelled. As an additional benefit of this method of restraining the implant 50, the tensioning member 1520 may be used to steer the implant 50 into the nuclear space 24. With the tensioning member 1520 pulled taught and threaded through the implant 50, the tensioning member 1520 can be used to steer the implant 50 into the predetermined location within the nuclear space 24 as the implant 50 is inserted. This reduces the need for insertion instruments having implant steering features. Although the retention features of this implant retention device 1500 are shown as being incorporated into the top shell 52 of the implant 50, it should be noted that the features may be alternatively incorporated into the bottom shell 54.

By one optional approach, the implant may include a plug 1532 or self locking crimp located within or adjacent an end 1540 of the longitudinal hole 1530 at the leading end 58 of the top shell 52 of the implant 50, wherein as soon as the implant 50 reaches a predetermined position within the nuclear space 24, the plug 1532 will compress down on the tensioning member 1510. The end 1540 of the elongated hole 1530 is enlarged and sized to accommodate the plug 1532. The plug 1532 has a plurality of concentric ridges 1534 along its length such that it may be press fit into the leading end 1540 of the longitudinal hole 1530, with the ridges resisting removal from the longitudinal hole 1530. The retaining plug 1532 has a hole 1536 therethrough such that the tensioning member 1510 may extend through the retaining plug 1532. The tensioning member 1510 and harpoon 1520 utilized should have a tensile strength adequate to restrain the implant in its predetermined position.

As illustrated in FIGS. 5-10, the implant retention device 1600 may also be in the form of a rigid or semi-rigid rod 1610 projecting directly from the implant. In this case, the trailing end 1612 of a rod 1610 is configured to snap into a snap joint in the implant, such as an elongated recess 1632 in the top perimeter surface of the leading end 58 of the bottom shell 54 of the implant 50. The recess 1632 has a generally circular cross-section to accommodate the rod 1610. The trailing end portion 1612 of the rod 1610 is then press or snap fit into the recess 1632. The rod 1610 and recess 1632 are sized such that the rod 1610 will tightly engage with the recess 1632 and be secured therein. The rod 1610 preferably has areas of increased diameter on either side 1614, 1616 of the trailing end portion 1612 to limit lateral movement of the rod 1610 such that the rod 1610 does not slide out of the elongated recess 1632. Thus, the trailing end portion 1612 has a reduced diameter as compared to the terminal trailing end 1614 and the remaining length 1616 of the rod 1610. The bottom shell 54 may have a corresponding cavity 1634 to accommodate the increased diameter of the terminal trailing end 1614.

Figure 5:
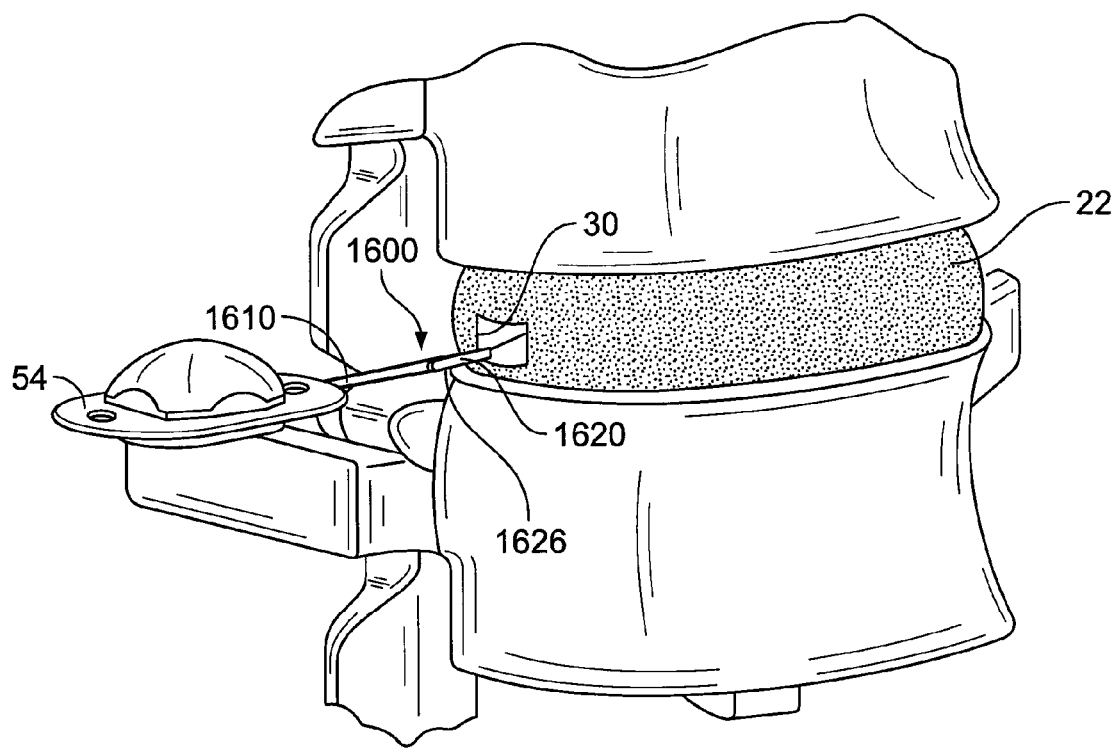
FIG. 5 is a perspective view of a second embodiment of an implant retention device secured to a bottom shell of the nuclear implant before insertion into a nuclear space of a spinal section.
Figure 6:
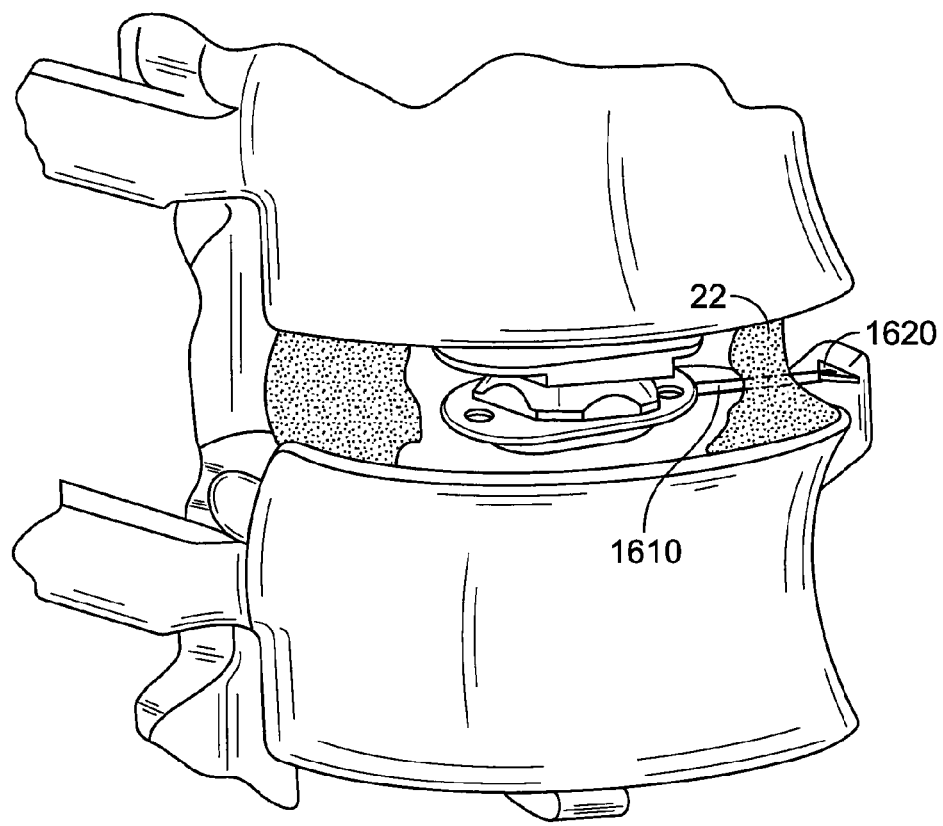
FIG. 6 is a perspective view of the implant retention device of FIG. 5 after insertion into the nuclear space of the spinal section and implantation in the annular wall.
Figure 7:
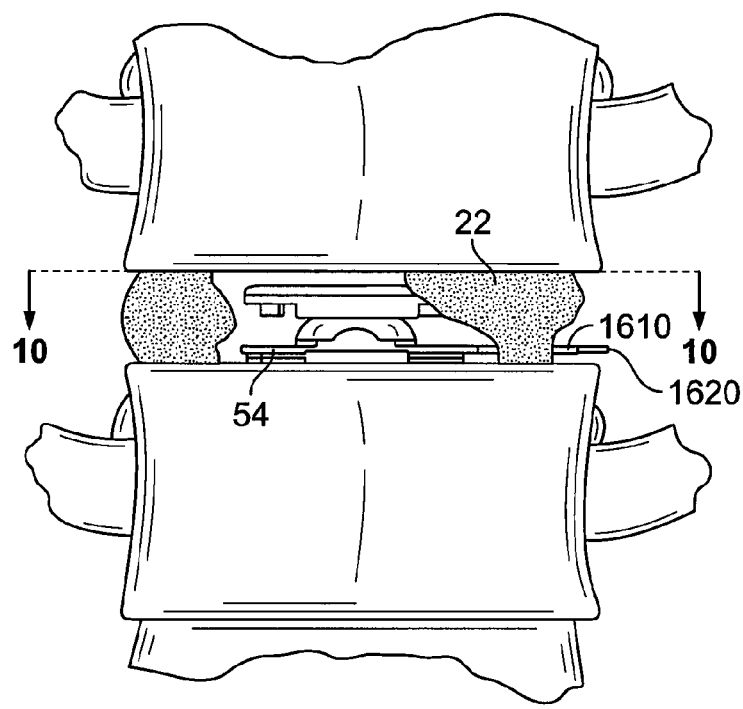
FIG. 7 is a partial front view of the spinal section of FIG. 6 showing the nuclear implant with the implant retention device attached thereto.
Figure 8:
FIG. 8 is a side view of the tensioning member of the implant retention device of FIG. 7.
Figure 9:
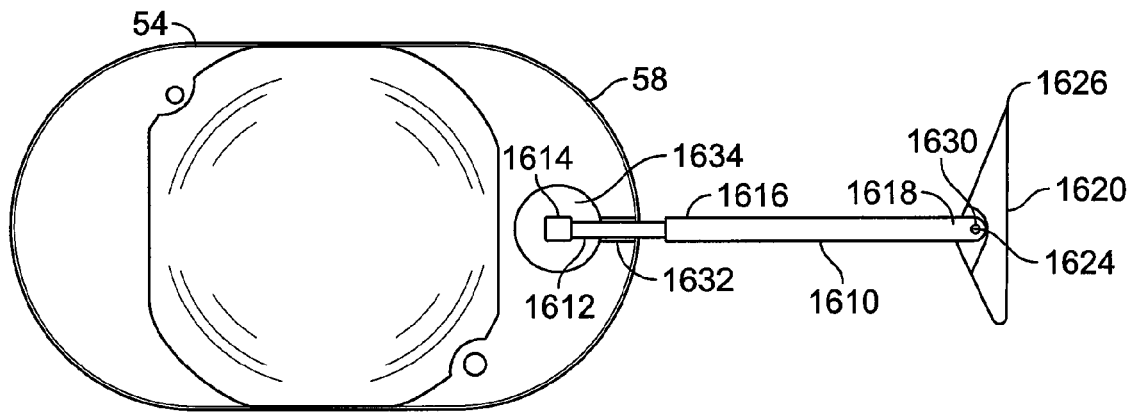
FIG. 9 is a top view of the bottom shell of the nuclear implant of FIG. 7 with the implant retention device secured thereto.
Figure 10:
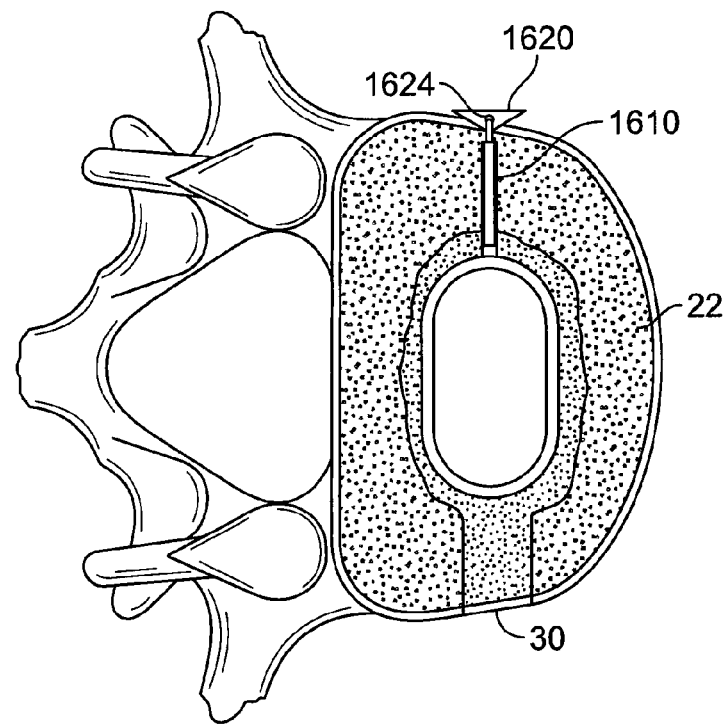
FIG. 10 is a cross-sectional top view of the spinal section of FIG. 7 taken along line 10-10 thereof and showing the nuclear implant with the implant retention device attached thereto.

The leading end 1618 of the rod 1610 is configured with a barb 1620, wherein the barb may include a harpoon or other anchoring means. The leading end 1618 of the rod 1610 has a forked configuration, with the barb 1620 positioned between the forked ends 1622 of the rod 1610. The barb 1620 is preferably pivotally mounted to the leading end 1618 of the rod 1610, such as with a pin 1624 extending through corresponding holes 1630 in the forked ends 1622 of the rod 1610 and the barb 1620. The barb 1620 is configured to engage with the annulus 22 to restrain the rod 1610 and thus the implant 50 in a predetermined position. For example, the barb 1620 in FIGS. 5-10 is a triangular shaped barb that pivots at the leading end 1618 of the rod 1610. The barb 1620 leads with a pointed edge 1626 as it is pushed through the annulus 22, as shown in FIG. 5 and then rotates to a transverse orientation with the rod 1610 when pulled backwards to engage with the annulus, as shown in FIG. 10, such that the longitudinal axis of the barb 1620 is transverse to the rod 1610. The barb 1620 may be pushed completely through the annulus 22 to ultimately rest against the outer annulus wall, or may rest somewhere within the annular wall 22. The barb 1620 is preferably embedded in an area of the annulus 22 generally opposite the annular opening 30. The implant 50 is tethered to the annulus 22 by the rod 1610 such that the implant 50 resists being expelled through the annular opening 30. With this configuration, the insertion of the implant 50 into the nuclear space 24 and activation of the implant retention device 1600 occurs simultaneously. Although the rod 1610 is shown as being connected to the bottom shell 54 of the implant 50, it is understood that the rod 1610 may be secured to the top shell 52, with the top shell 52 being configured to engage with the rod 1610.

Figure 11:
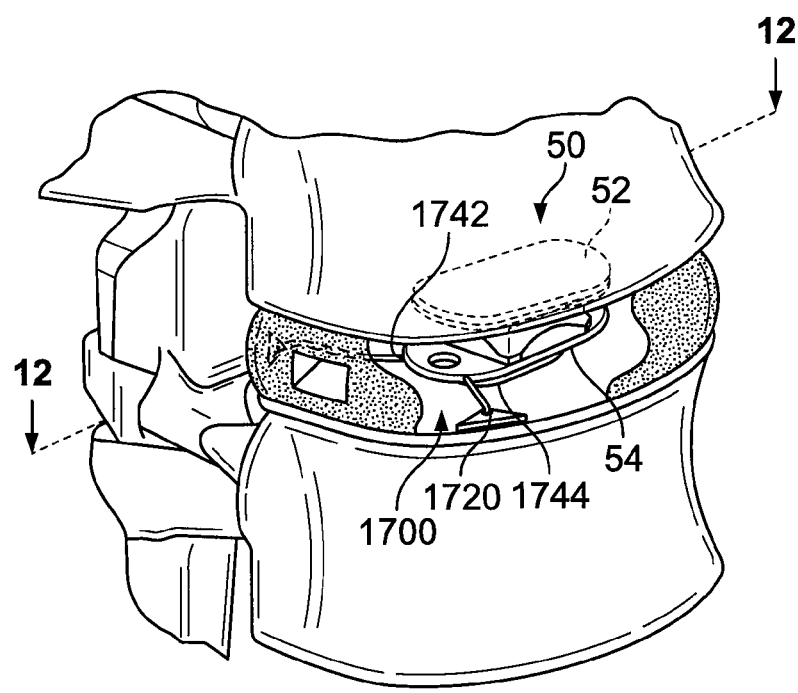
FIG. 11 is a perspective view of a third embodiment of an implant retention device threaded through a nuclear implant and implanted in the annular wall, with the nuclear implant inserted in a nuclear space of a spinal section.
Figure 12:
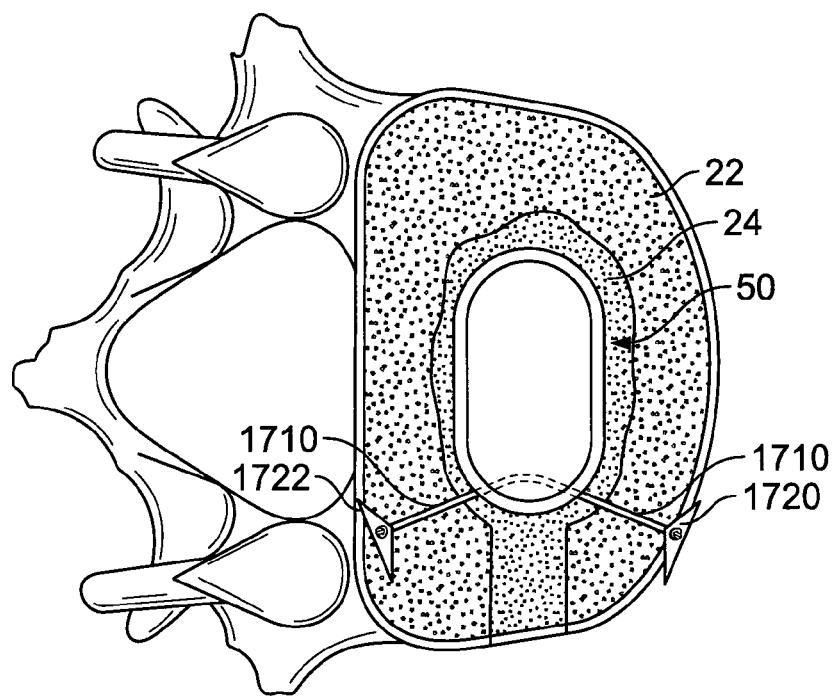
FIG. 12 is a cross-sectional top view of the spinal section of FIG. 11 taken along line 12-12 thereof and showing the nuclear implant with the implant retention device threaded therethrough.
Figure 13:
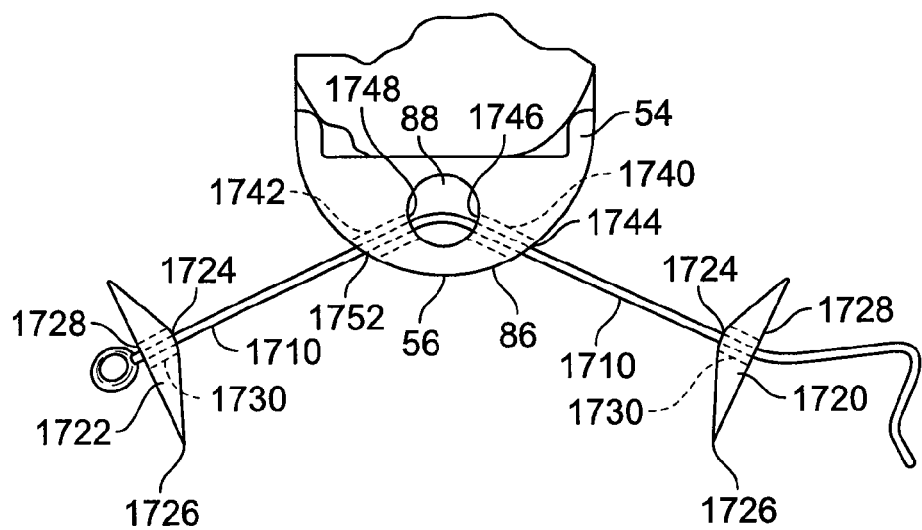
FIG. 13 is a fragmentary top view of the bottom shell of the nuclear implant of FIG. 12.

In yet another embodiment of an implant retention device 1700, the implant 50 includes an elongated tensioning member 1710 attachment feature near the trailing end 56 of the implant 50. As shown in FIGS. 11-13, the trailing end 56 of the bottom shell 54 of the implant includes 50 a pair of holes 1740, 1742, with each hole 1740, 1742 extending from the outer perimeter wall 86 of the bottom shell 54 through to a cavity 88 formed in the bottom shell 54. A pair of barbed anchors 1720, 1722 are embedded in the annular wall 22 on each side of the annular opening 30, with the barbed anchors 1720, 1722 being generally positioned at the same level as the holes 1740, 1742 in the bottom shell 54. The barbed anchors may alternatively comprise a harpoon or other anchoring mechanism. One anchor 1722 is mounted toward a posterior side of the annulus 22, with the other anchor 1720 mounted toward an anterior side of the annulus 22. The barbed anchors 1720, 1722 are preferably triangular in shape, with at least one sharp angular feature 1726 for penetrating the annular wall 22. As with the embodiment 1600 above, the anchor 1720 or 1722 is oriented such that the angular feature 1726 leads and is pushed through the inner wall of the annulus 22 using, for example, a tool or instrument. When the angular feature 1726 engages with the annular wall 22, the barbed anchor 1720, 1722 is then rotated and pulled backwards to engage the anchors 1720, 1722 with the annular wall 22, such that the longitudinal axis has a transverse orientation to the tensioning member 1710. The apex 1724 of the triangle-shaped barbed anchor 1720, 1722 extends toward the implant 50 once the anchors 1720, 1722 have been secured in the annulus 22.

To secure the implant 50 using the nuclear retention device 1700, an elongated tensioning member 1710, such as a wire, cable, or suture, is threaded through the implant 50, and then connected at each end to one of the anchors 1720, 1722. More specifically, an end of the tensioning member 1710 is inserted through the external end 1744 of the hole 1740 in the bottom shell 54 that is adjacent the anterior anchor 1720 and threaded through to the internal end 1746 of the hole 1740 in the cavity 88 of the bottom shell 54. The tensioning member 1710 is then threaded back through the internal end 1748 of the other hole 1742 such that the tensioning member 1710 exits the external end 1752 of the hole 1742 and extends away from the implant 50. Alternatively, the tensioning member 1710 may be secured to the implant 50 using another anchoring mechanism or hole arrangement. By another optional approach, the tensioning member 1710 may be threaded through the implant 50 and then the anchors 1720, 1722 are secured to ends of the tensioning member 1710. With the implant 50 positioned within the nuclear space 24, each anchor 1720, 1722 can then be engaged with the annular wall 22 by orienting each anchor 1720, 1722 such that its longitudinal axis is generally parallel to the tensioning member 1710, then inserting the anchor into the annulus 22, and then rotating the anchor such that the longitudinal axis of the anchor 1720, 1722 is generally transverse to the tensioning member 1710. In addition, although a single tensioning member 1710 is shown for this embodiment, the tensioning member 1710 may comprise a tensioning member associated with each anchor 1720, 1722, with each tensioning member secured at one end to an anchor and at another end to the implant.

Each end of the tensioning member 1710 is threaded through a hole 1730 in each anchor 1720, 1722 to create a pivotal connection between the anchor 1720, 1722 and the tensioning member 1710. The hole 1730 in the anchors 1720, 1722 extends through the length of the anchor from the apex 1724 of the triangle-shaped anchors 1720, 1722 facing the implant 50 to an edge 1728 of the anchors 1720, 1722 opposite the apex 1724. Alternatively, the hole 1730 may extend through the width of the anchors 1720, 1722. The ends of the tensioning member 1710 are then secured to the anchors 1720, 1722 or tied off so as to secure the ends of the tensioning member 1710 to the anchors 1720, 1722. This retention system again prevents the implant 50 from being expulsed through the annular opening 30 by tethering the implant 50 to the annulus 22. This implant retention device 1700 may be alternatively configured to attach to the top shell 52 of the implant 50.

Figure 14:
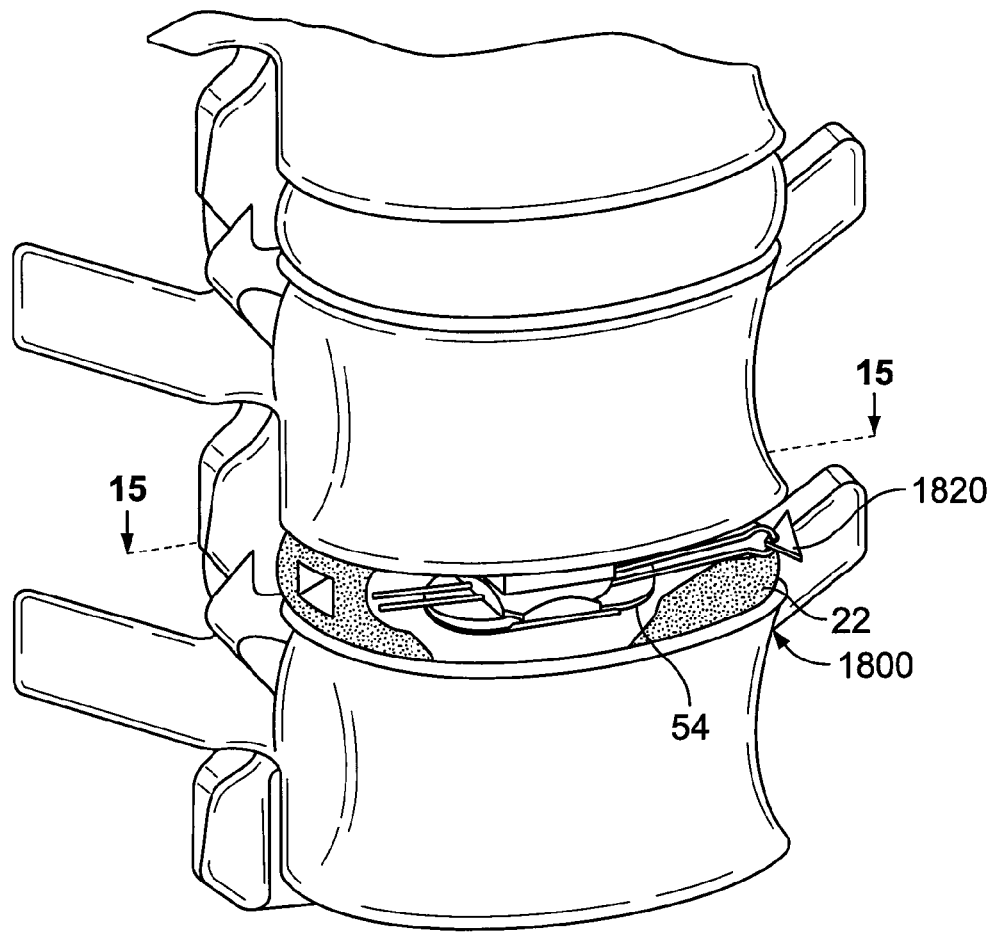
FIG. 14 is a perspective view of a fourth embodiment of an implant retention device threaded through a nuclear implant and implanted in the annular wall, with the nuclear implant inserted in a nuclear space of a spinal section.
Figure 15:
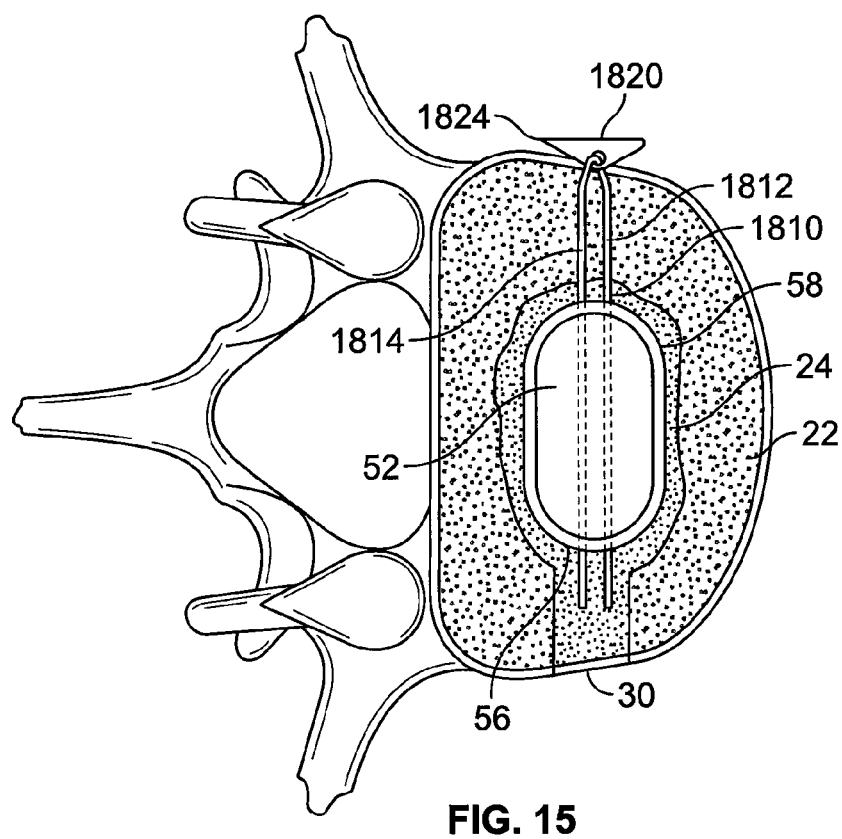
FIG. 15 is a cross-sectional top view of the spinal section of FIG. 14 taken along 15-15 thereof and showing the nuclear implant with the implant retention device threaded therethrough.
Figure 16:
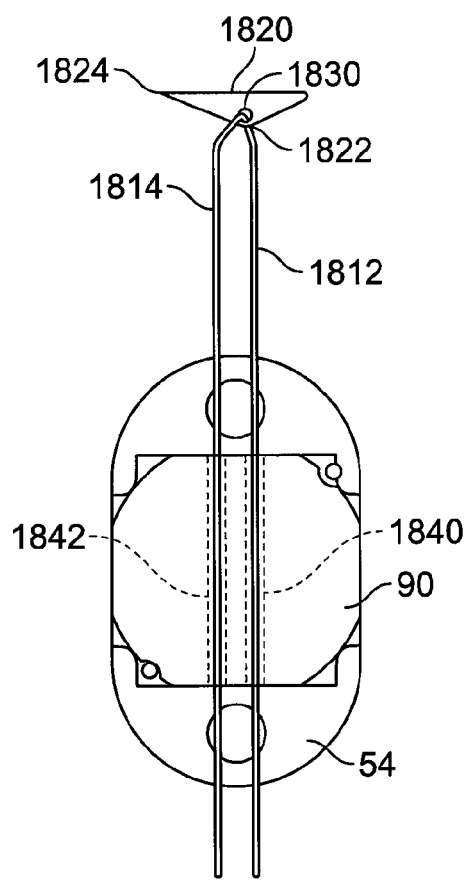
FIG. 16 is a top view of the lower shell of the nuclear implant of FIG. 14 with the implant retention device threaded therethrough.
Figure 17:
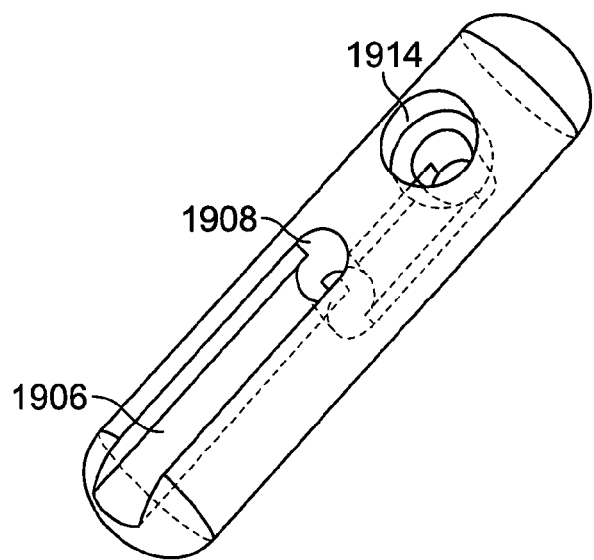
FIG. 17 is a perspective view of a fifth embodiment of an implant retention device showing an elongate bar anchoring device.
Figure 18:
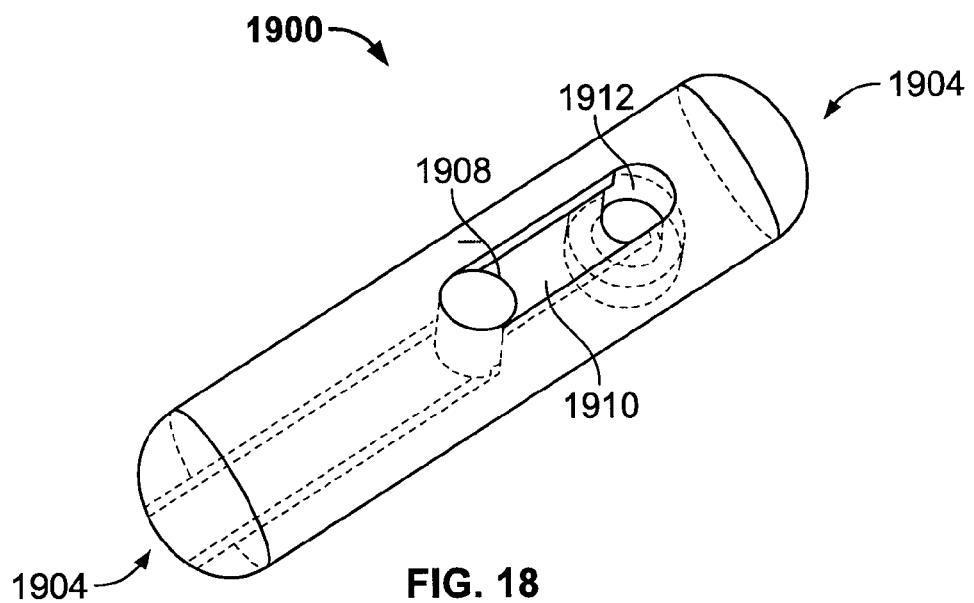
FIG. 18 is a second perspective view of the anchoring device of FIG. 17.
Figure 19:
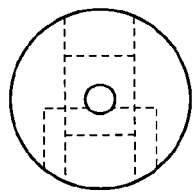
FIG. 19 is an end view of the anchoring device of FIG. 17.
Figure 20:
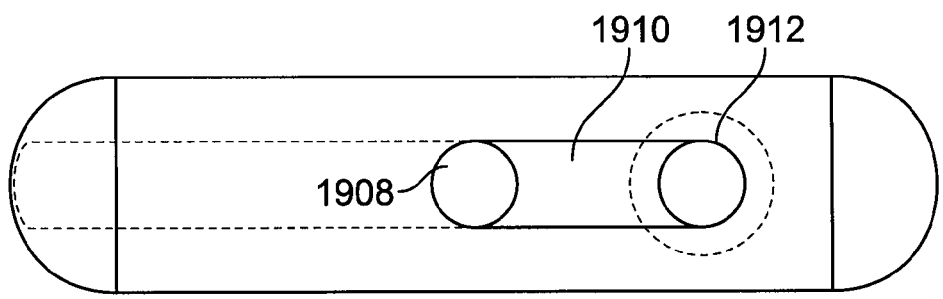
FIG. 20 is a top view of the anchoring device of FIG. 17.
Figure 21:
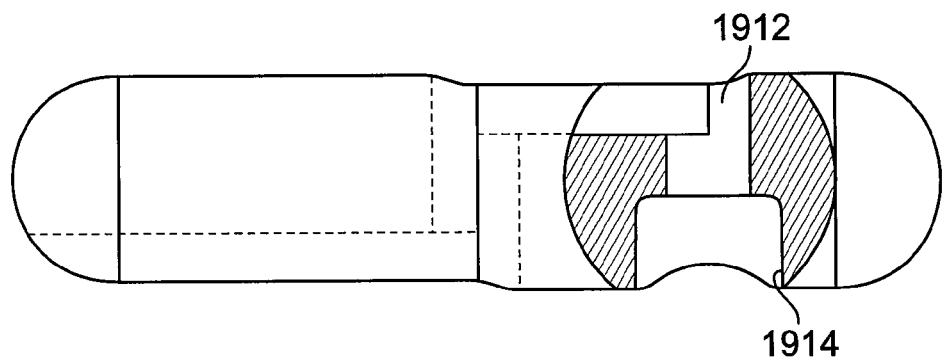
FIG. 21 is a side view of the anchoring device of FIG. 17.
Figure 22:
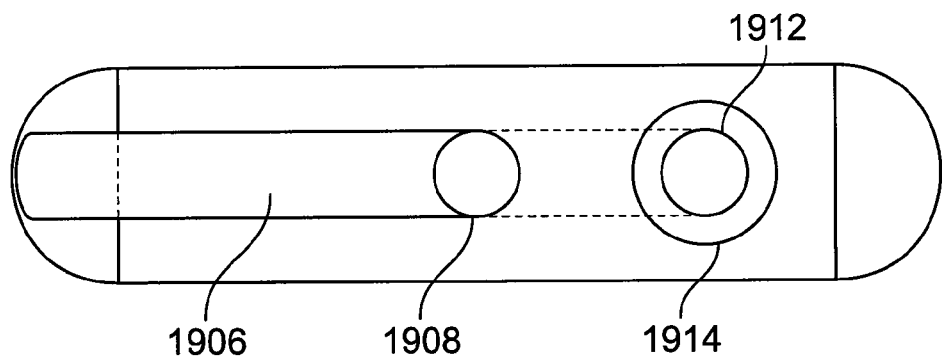
FIG. 22 is a bottom view of the anchoring device of FIG. 17.
Figure 23:
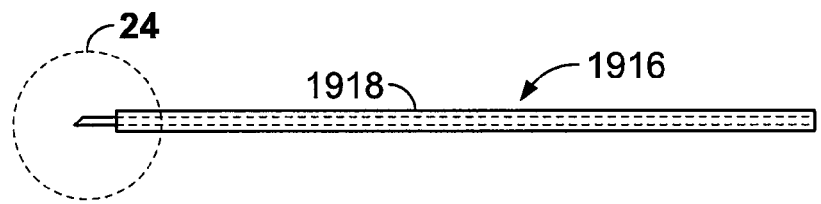
FIG. 23 is a side view of a first embodiment of an anchoring device insertion tool.
Figure 24:
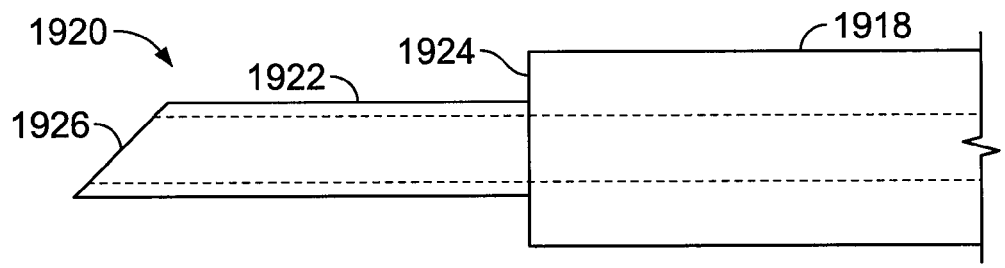
FIG. 24 is an enlarged partial side view of the insertion tool of FIG. 23.
Figure 25:
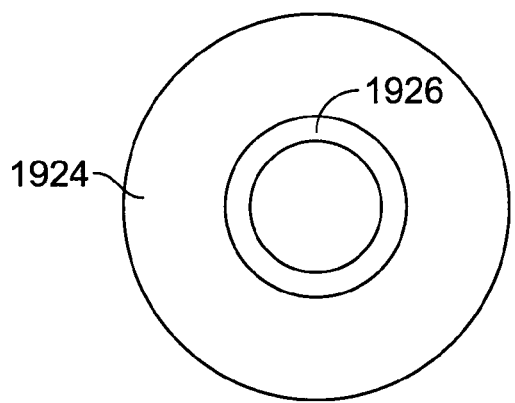
FIG. 25 is an end view of the insertion tool of FIG. 23.

FIGS. 14-16 illustrate an alternative embodiment. In this embodiment of a nuclear retention device 1800, a harpoon 1820 is disposed generally centrally along the length of a tensioning member 1810. The tensioning member 1810, such as a cable, suture, or wire, for example, is threaded through a through hole 1830 in the apex 1822 of the triangle-shaped harpoon 1820 to pivotally connect the tensioning member 1810 to the harpoon 1820. The harpoon 1820 may alternatively comprise a barbed anchor or other anchoring mechanism. The harpoon 1820 is disposed generally centrally along the length of the tensioning member 1810, such that the tensioning member is doubled against itself and divided into an anterior-side tensioning member 1812 and a posterior-side tensioning member 1814. The harpoon 1820 is initially seated in the annular wall 22 using forceps or other instrument. Again, a sharp end 1824 of the harpoon 1820 is pushed through the annulus 22 from the interior of the nuclear space 24, with a longitudinal axis of the harpoon 1820 being generally parallel to the tensioning member 1810. The harpoon is then rotated to a transverse orientation when pulled backwards by the tensioning member 1810 to secure the harpoon 1820 in the annular wall 22. The harpoon 1820 is preferably embedded in an area of the annulus 22 generally opposite the annular opening 30. The harpoon 1820 may be pushed completely through the annulus 22 to ultimately rest against the outer annulus wall, or may rest somewhere within the annular wall 22.

In this embodiment, the implant 50 includes an anterior-side longitudinal hole 1840 and a posterior-side longitudinal hole 1842 extending through a portion of the bottom shell 54 of the implant 50 for threading the corresponding anterior-side tensioning member 1812 and posterior-side tensioning member 1814 therethrough. The two longitudinal holes 1840, 1842 are preferably formed through the domed portion 90 of the bottom shell 54. The tensioning members 1812, 1814 are threaded through the corresponding holes 1840, 1842 in the implant 50, with the tensioning members 1812, 1814 being used to steer the implant 50 such that the implant 50 is seated in its predetermined position within the nuclear space 24. The free ends of the tensioning members 1812, 1814 may then be tied off, crimped, or otherwise secured by the surgeon as he works through the annular opening 30. Again, the longitudinal holes 1840, 1842 may be alternatively formed through the top shell 52 of the implant 50.

In an alternate embodiment shown in FIG. 5 similar to the embodiments of FIGS. 17-36, the securing mechanism may take the form of an elongate bar 1900, instead of a harpoon or triangular barb. As opposed to the harpoon and other anchoring structure, the elongate bar 1900 may be provided with blunt or rounded ends 1904. The elongate bar's blunt edges 1904 are less likely to cause additional trauma to the annulus 22 once the bar 1900 is inserted in its final resting position. The elongate bar 1900 also provides internal structure that allows the tensioning member 1902 to pass through or within the body of the bar 1900, thereby streamlining and easing insertion. After insertion, the bar 1900 is easily pivoted transversely to the tensioning member 1902. The elongate bar 1900 is preferably cylindrical in shape with rounded ends 1904 and internal passages to allow the tensioning member 1902 to pass through the bar 1900. The bar 1900 has a channel 1906 extending from one end in the longitudinal direction terminating at a central throughbore 1908. At the opposite end of the central throughbore 1908, a second channel 1910 extends between the central throughbore 1908 and a peripheral throughbore 1912, which extends through the bar 1900 to the other side of the bar 1900. At the terminating end of the peripheral throughbore 1912 is an enlarged recess 1914 in which the tensioning member 1902 may be knotted or otherwise secured, without protruding from the outer profile of the bar 1900. Although the throughbores are shown having orientations that are substantially parallel to each other, it is understood that the throughbores may be angled with respect to one another, such that one or both throughbores may be skewed with respect to the longitudinal axis of the bar. The tensioning member 1902 passes from its fastened end in the enlarged recess 1914, through the peripheral throughbore 1912, along the second channel 1910 and through the central throughbore 1908. When the elongate bar 1900 is in the insertion position, that is, longitudinally aligned with the insertion direction through the annulus 22, the tensioning member 1902 is disposed within the channel 1906. The bar 1900 is preferably made of PEEK, but may be made with any other suitable biocompatible material. In addition, the bar may be made from a bioresorbable material, such as NanOss™, produced by Angstrom Medica, Inc.

Figure 26:
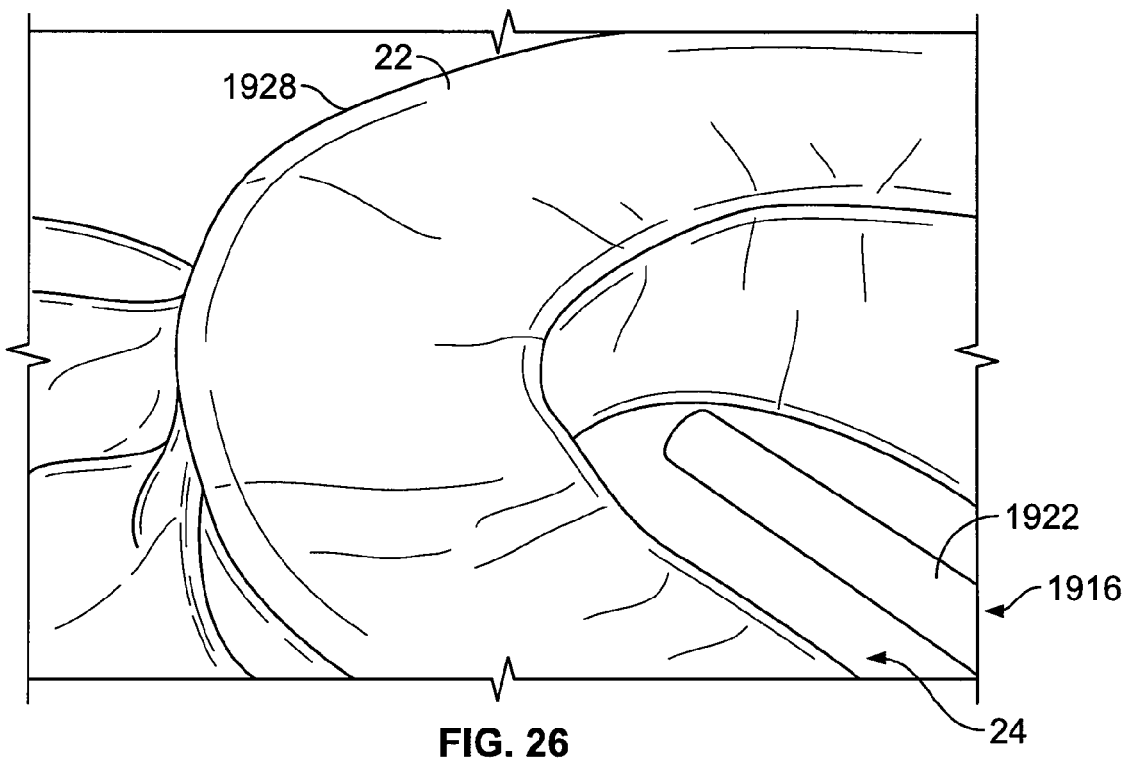
FIG. 26 is an enlarged perspective view of a second embodiment of the insertion tool showing the tool within the nuclear space of an intervertebral disc.
Figure 27:
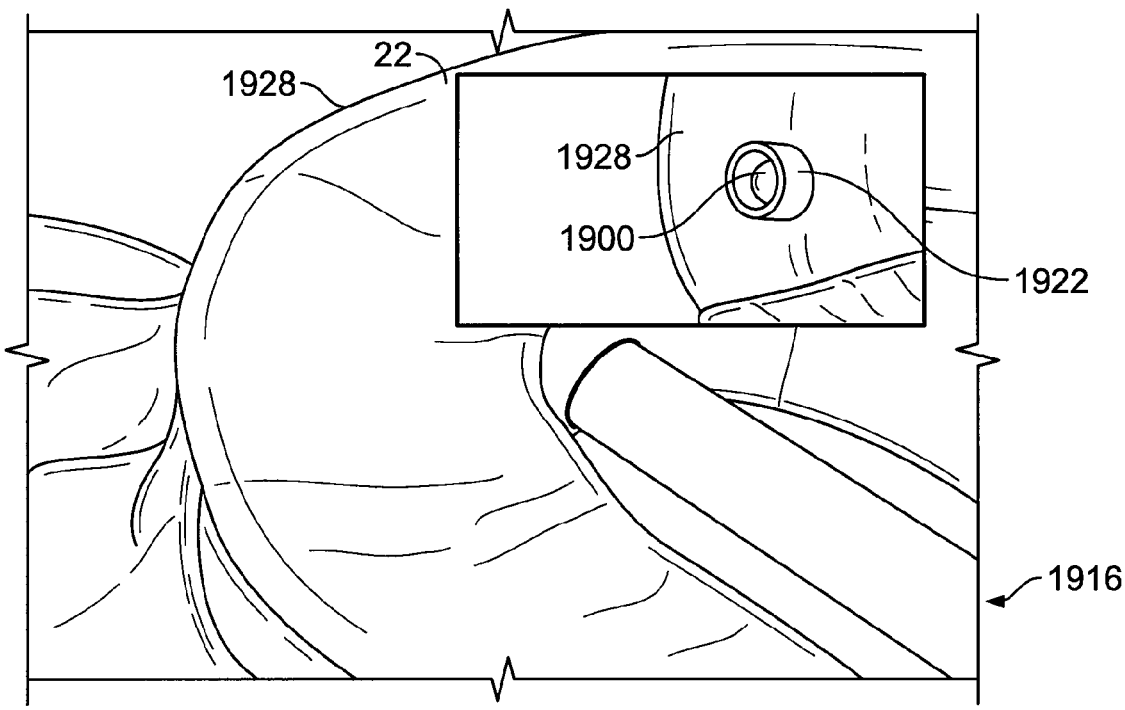
FIGS. 27-30 are enlarged perspective views of the insertion tool of FIG. 26 inserting the anchoring device through the annular wall with an inset enlarged perspective view of the outer annular wall showing the setting of the anchoring device of FIG. 17.
Figure 28:
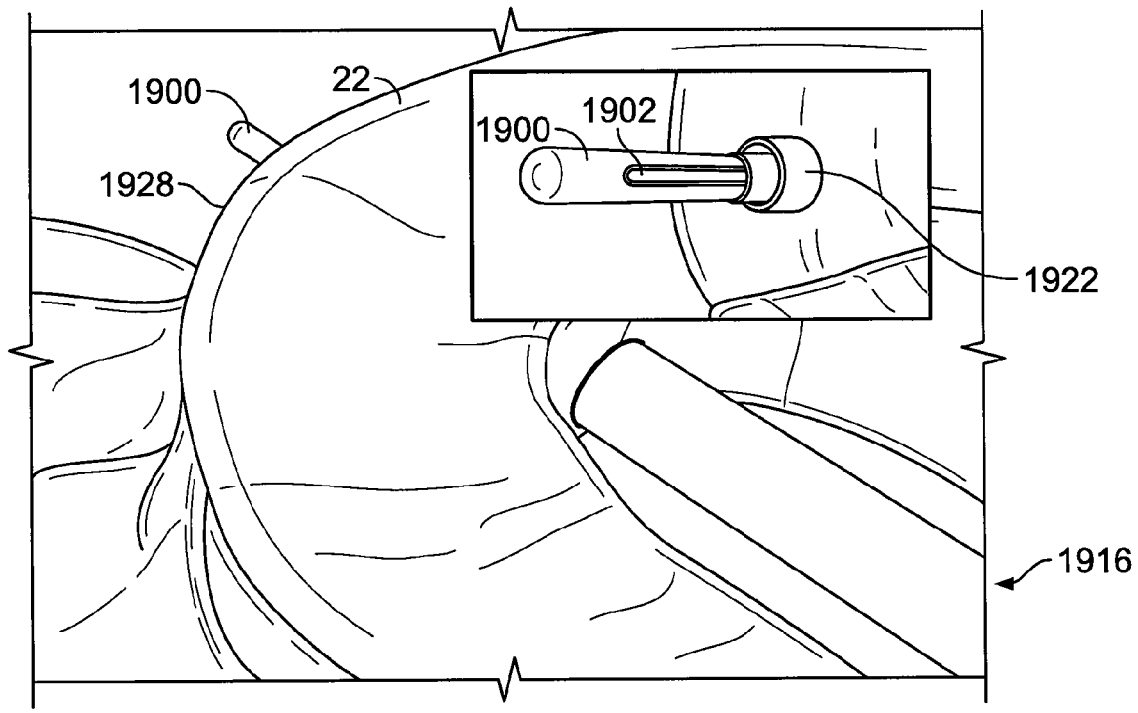
Figure 29:
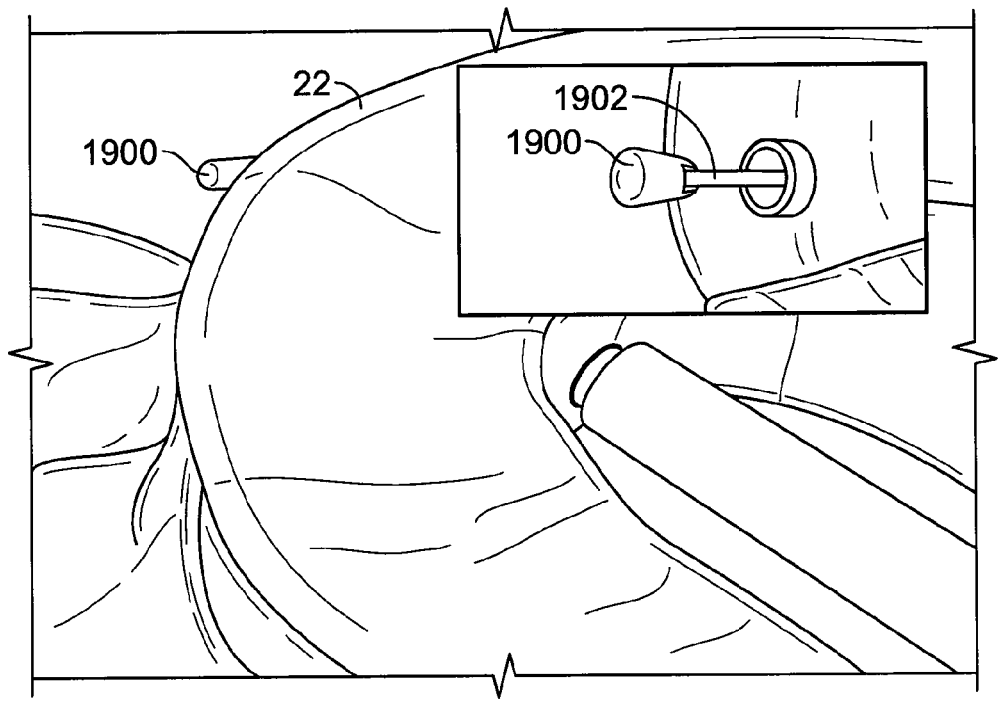
Figure 30:
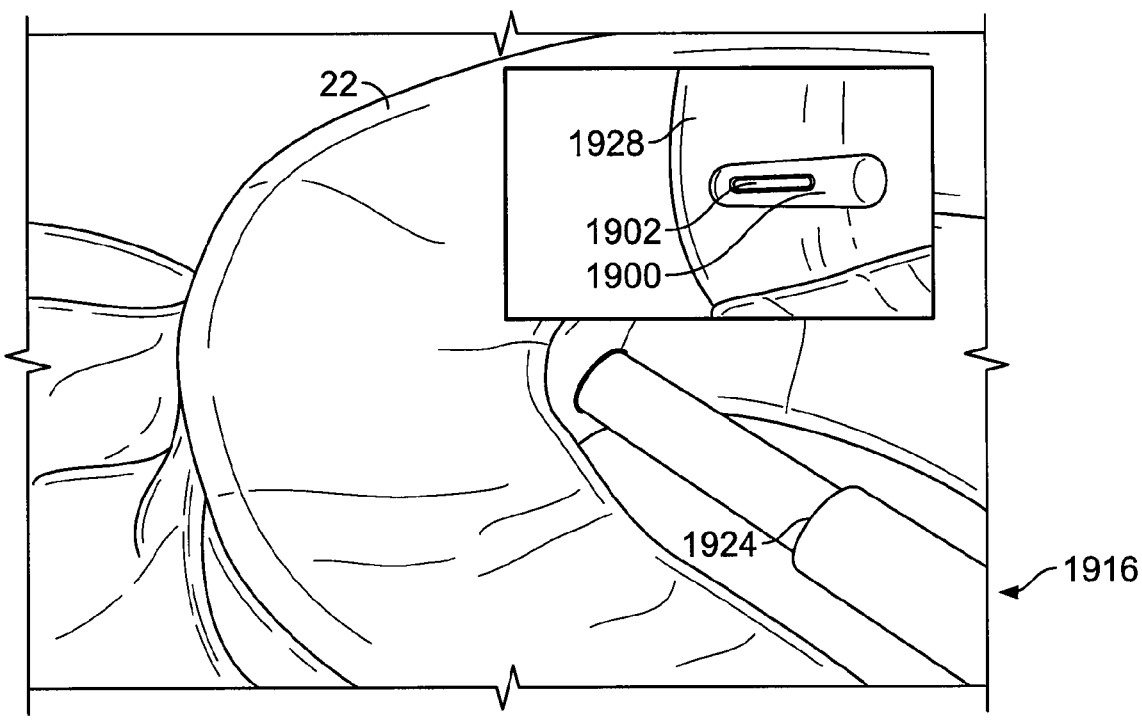
Figure 31:
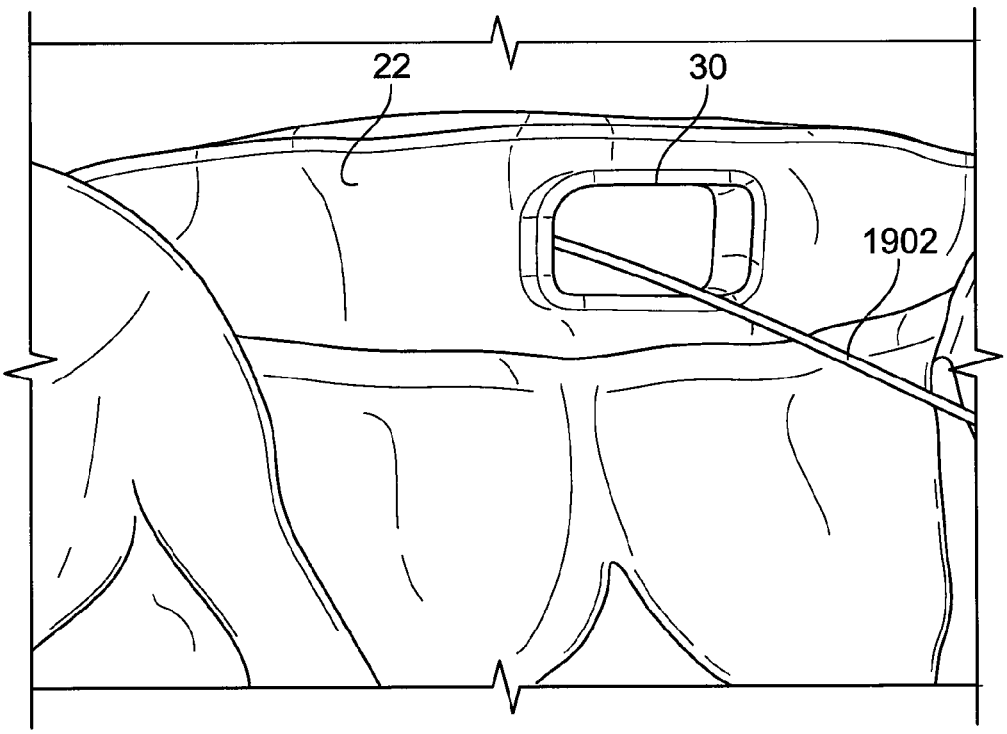
FIG. 31 is a perspective view of a spinal section showing an opening in the annular wall with a tensioning member extending therethrough.
Figure 32:
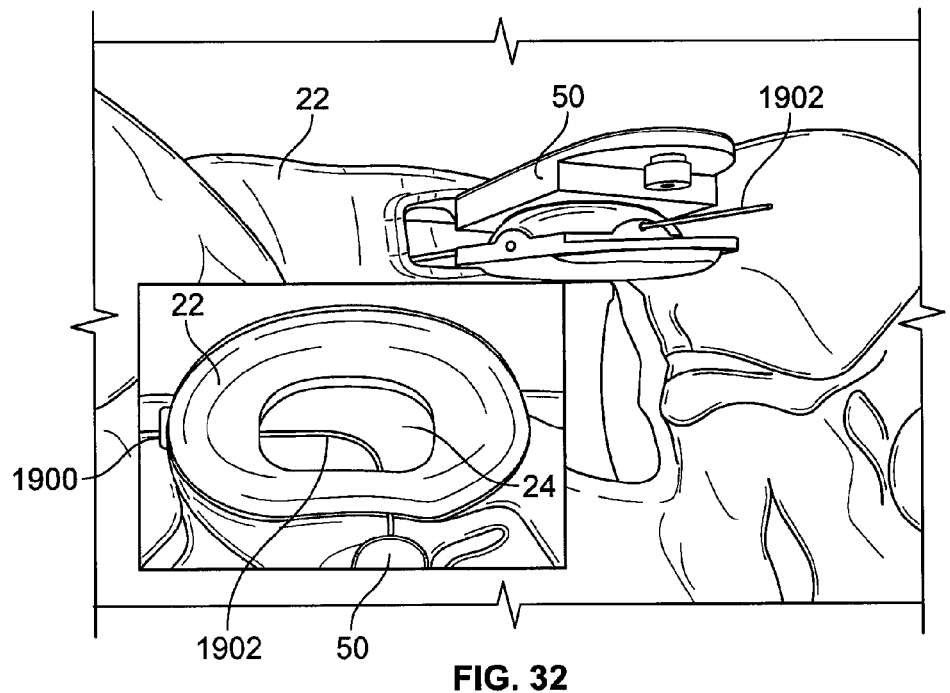
FIGS. 32-35 are perspective views of a nuclear implant being guided along the tensioning member into the nuclear space, with an inset top view of a spinal section showing the progress of the implant.
Figure 33:
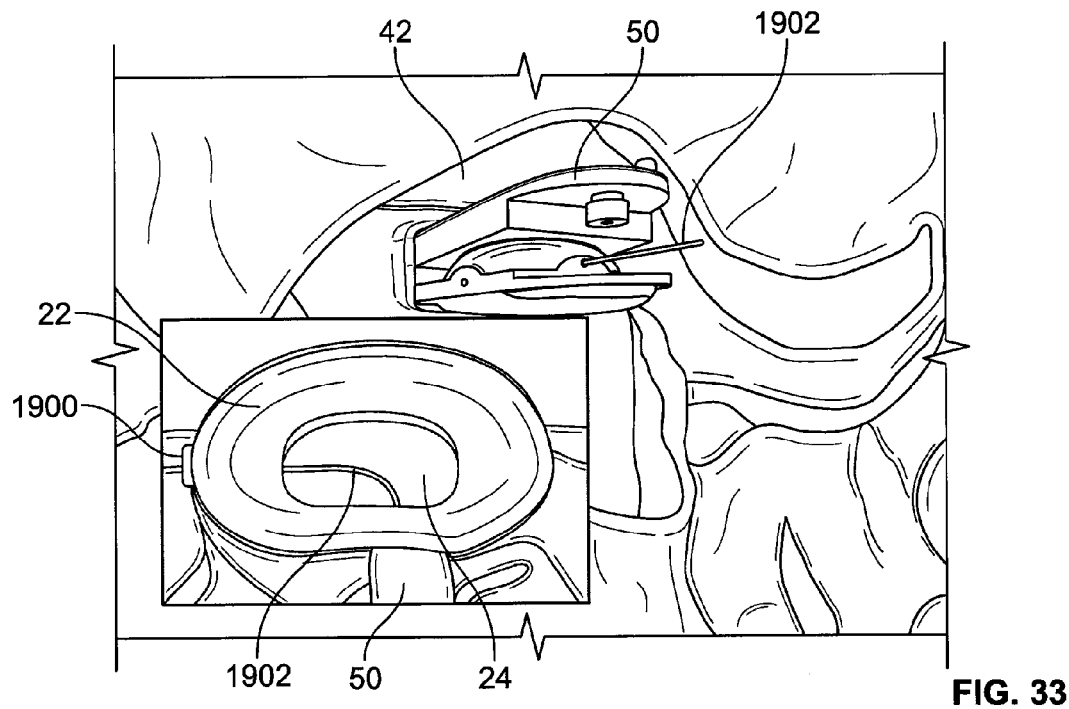
Figure 34:
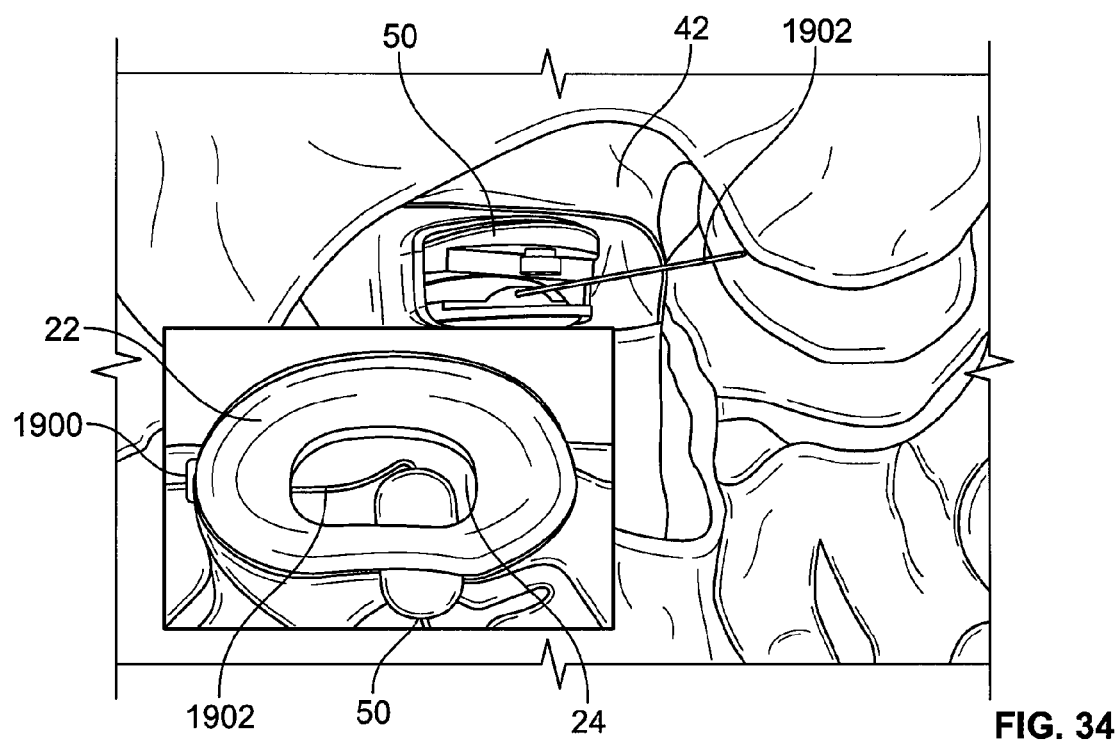
Figure 35:
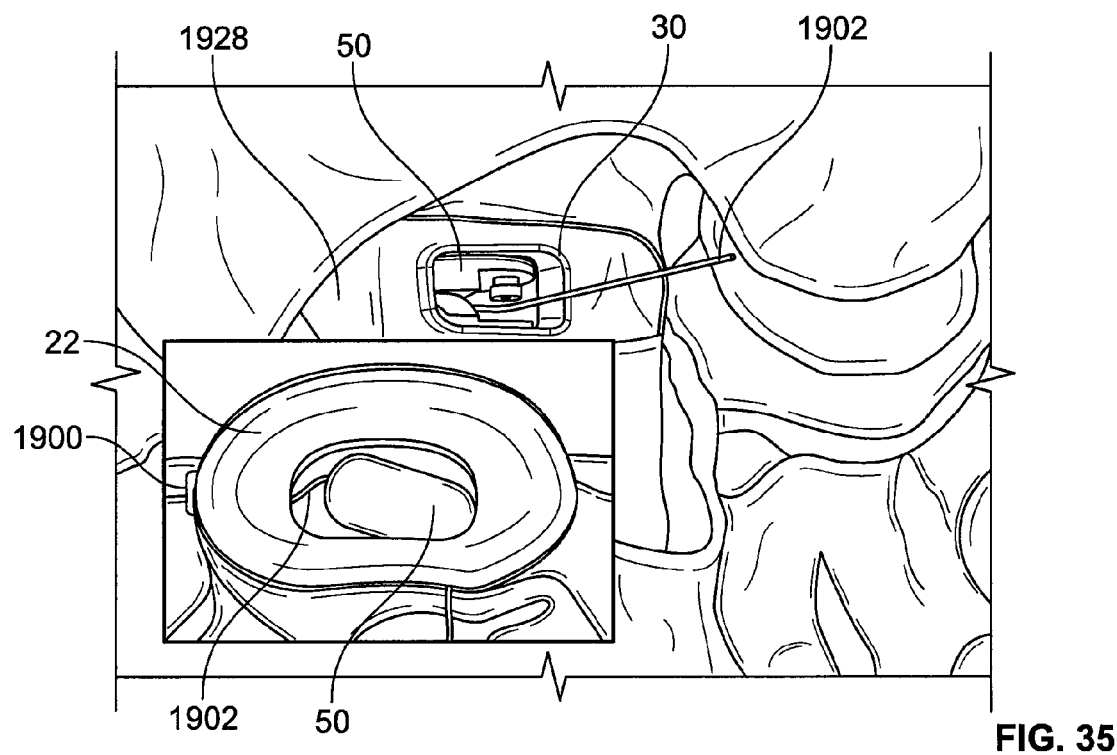
Figure 36:
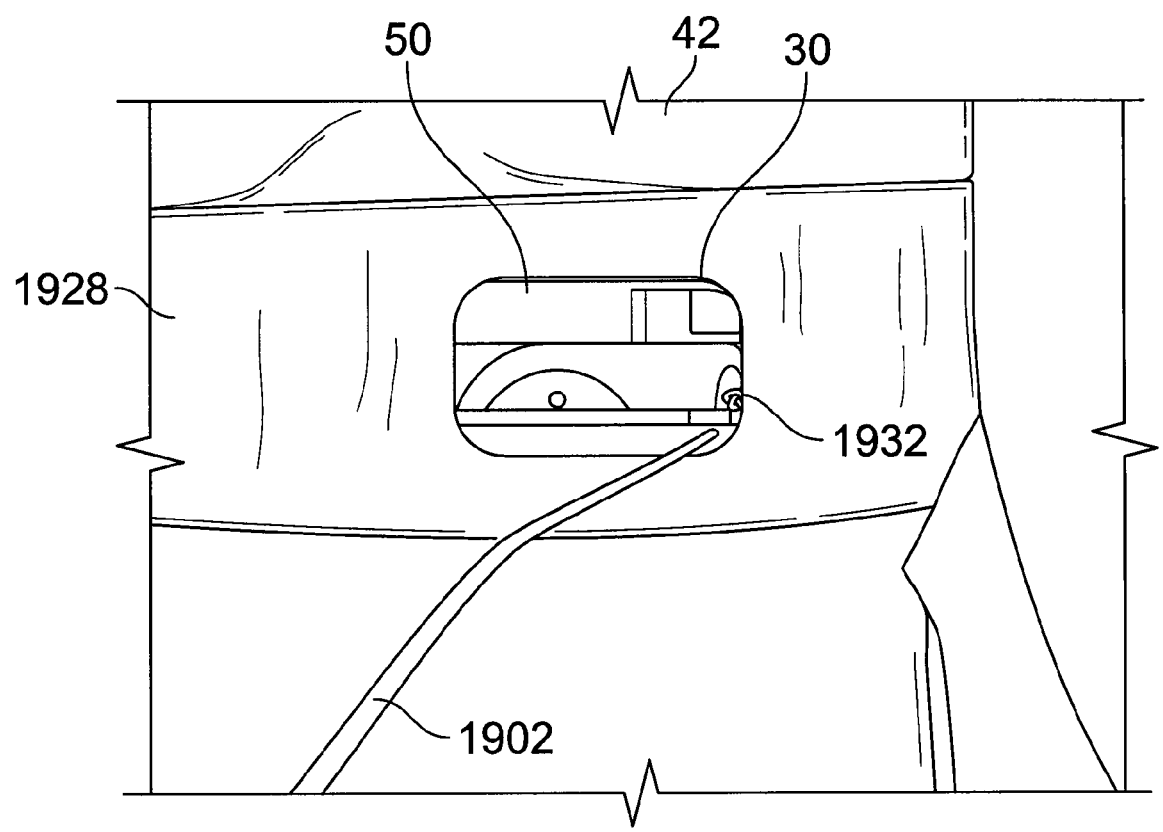
FIG. 36 is an enlarged perspective view of the spinal column of FIG. 31 showing, a knot fastening the tensioning member to the implant.

To insert and install the elongate bar 1900, an insertion tool 1916 is implemented, as shown in FIGS. 23-36. In one embodiment, the insertion tool 1916 is a cannulated elongate shaft 1918 having a distal end 1920 with an insertion tip 1922 and a shoulder spaced 1924 from the distal end 1920. The insertion tip 1922 may have a beveled or sharpened end 1926 to promote insertion through the annular wall 22. The shoulder 1924 is provided to limit how far the insertion tip 1922 may travel through the wall 22 by providing a confronting surface that abuts the inner annular wall once the tip 1922 is fully inserted. Prior to insertion, the tensioning member 1902 is attached to the elongate bar 1900. Then, the elongate bar 1900 is inserted into the cannulated shaft 1918 and positioned at the tip 1922 of the shaft 1918. Next, as shown in FIGS. 26 and 27, the insertion tool 1916 is inserted into the nuclear space 24 through a window 30 in the annular wall 22, and the tip 1922 is pushed through the annular wall 22. Once the insertion tip 1922 fully protrudes through the wall 22, the elongate bar 1900 is pushed distally through the tip 1922 until it is completely expelled from the insertion tool 1916 (FIG. 28). The tool 1916 is then retracted from the wall 22 and removed from the nuclear space 24 leaving the elongate bar 1900 positioned adjacent the outer annular wall 1928 (FIGS. 29 and 30). The tensioning member 1902 protrudes through the passage in the wall 22 created by the insertion tool 1916 and out through the annular window 30 (FIG. 31). The tensioning member 1902 is then pulled taught, causing the bar 1900 to be pulled against the outer annular wall 1928 and positioned in a transverse orientation to the tensioning member 1902. As shown in FIG. 32, the free end of the tensioning member 1902 may then be threaded through a guide portion on the implant 50 such as a longitudinal hole 1530 (FIG. 3) to help guide the implant 50 through the annular window 30 and into the nuclear space 24. Depending on where the securing mechanism is positioned in relation to the annular window 30, the tensioning member 1902 may help steer the implant 50 into position, such that the leading end of the implant 58 will follow the tensioning member 1902 towards the securing mechanism 1902. As shown in FIGS. 33-35, the elongate bar 1900 has been secured in a lateral portion of the annulus 22 while the window 30 is disposed posteriorly. Therefore, as the implant 50 is inserted into the nuclear space 24, it is guided from its insertion orientation, which is anterior-posterior, to its implanted orientation, which is generally lateral. Once the implant 50 is in position within the annulus 22, the free end of the tensioning member 1902 is fastened to the implant 50, thereby keeping the implant 50 from being expelled through the annulus 22. In a preferred embodiment, a slip knot 1932 is used to fasten the tensioning member 1902 to the trailing end of the implant 56 as shown in FIG. 36. The insertion tool 1916 may have an adjustable distal portion, such that the tip 1922 may be positioned at an angle with respect to the body of the tool 1916. This feature allows the tool 1916 greater maneuverability and is helpful to position the securing mechanism at a desired position in the annulus 22, especially when the desired anchoring position is not directly across from the annular window 30. This method of insertion may also be implemented with any of the other embodiments disclosed. Additionally, the insertion tool 1916 can be adapted to be implemented with any of the other anchoring devices.

Figure 37:
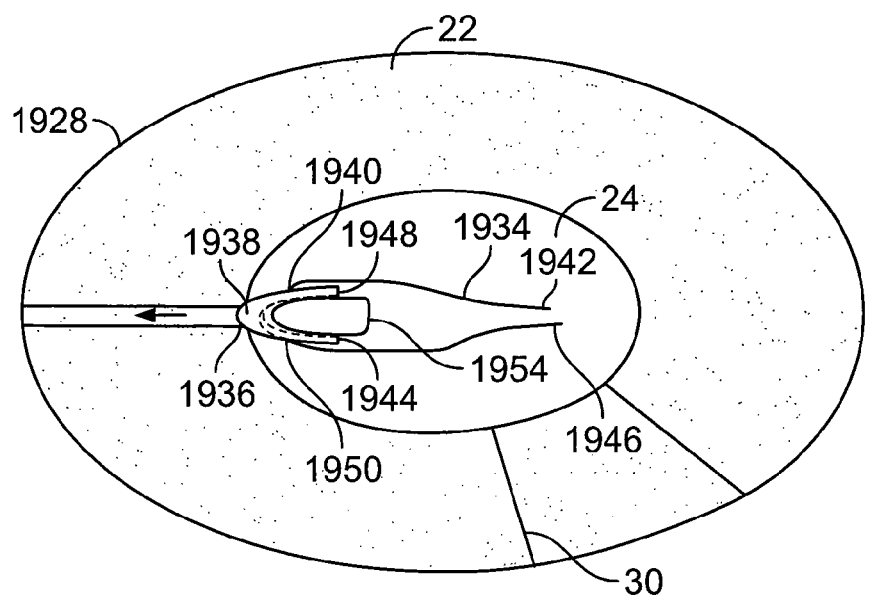
FIG. 37 is a top view of a sixth embodiment of an implant retention device showing a flexible anchoring device with a suture extending through a thicker hollow member being pulled through the annular wall.
Figure 38:
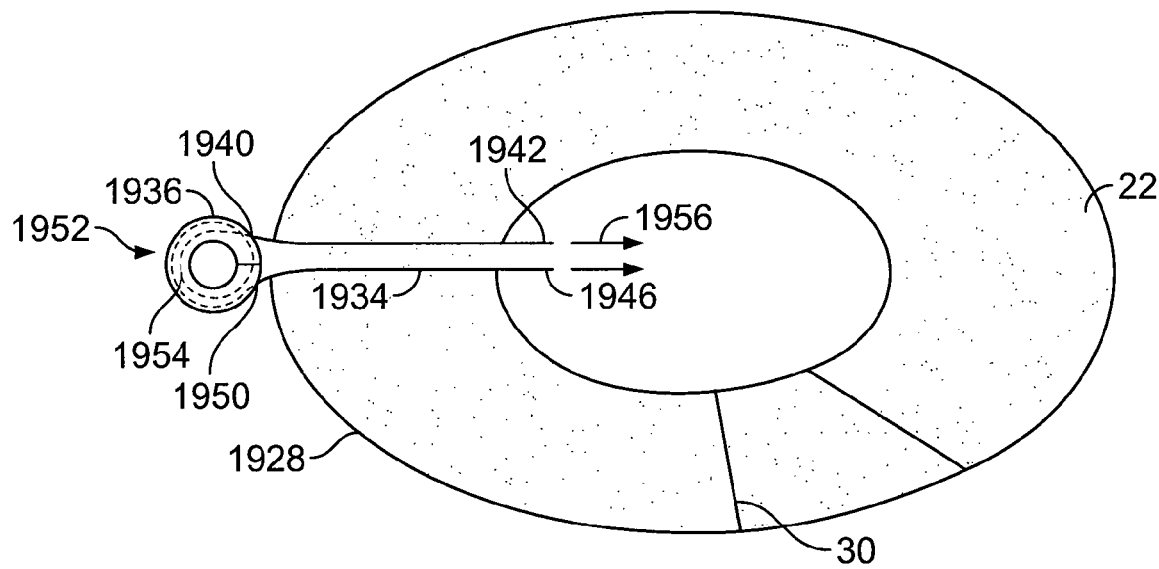
FIG. 38 is a top view of the flexible anchoring device of FIG. 37 with the suture pulled taught to engage the flexible anchoring device with the annular wall.

In another embodiment, the securing mechanism may be in the form of a flexible anchor. As used herein, flexible does not necessarily mean that the anchor is pliable or resilient. The term flexible is meant to encompass the physical characteristics of objects such as sutures, wires, strings, cables, and the like, as well as resilient materials, such as certain metals, polymers, and other known resilient materials. Flexible anchors are advantageous because they can be inserted into or through the annular wall with minimal trauma to the annulus 22. In a preferred embodiment shown in FIGS. 37 and 38, the tensioning member 1902 in the form of a suture 1934, is threaded through a hollow member 1936 in a manner that causes the member to compress or bunch up when the tensioning mechanism 1902 is pulled away from the hollow member 1936. The hollow member 1936 is preferably formed from a braided #2 suture that has been cored to create a central passage 1938 through the suture. The tensioning member 1902 has a smaller diameter than the hollow member 1936, and is preferably a 2-0 monofilament suture. However, alternative materials may be suitable as will be apparent to those skilled in the art. To form the flexible anchor, a first end 1942 of the tensioning mechanism 1902 is threaded into an end 1944 of the hollow member 1936, pulled through an opening 1940 in the side wall of the hollow member 1936 near the opposite end 1948 from which the tensioning mechanism 1902 was inserted. The other end of the of the tensioning member 1946 is inserted through the other end of the hollow member 1948 and pulled through an opposing opening in the side wall 1950 in a corresponding manner to the first end of the tensioning member 1942. Effectively, the tensioning member 1902 forms a loop 1954 within hollow member 1936, with the free ends 1942, 1946 protruding through exit openings in the side walls 1940, 1950 of the hollow member 1936 positioned on the opposite end from the end that the respective free end of the tensioning member 1902 enters the hollow member 1936.

To install the flexible anchor 1952, a delivery instrument is implemented in the form of a needle or pin with sharpened entry end and a fastening portion, such as a hook, on the trailing end of the instrument. The hollow member and tensioning mechanism assembly is attached to the fastening portion, and the delivery instrument is fed through the annular window 30 and then pushed through the annular wall 22. Because the hollow member 1936 and suture 1934 are flexible, they will collapse or fold in on each other as they are pulled through the annulus 22 by the delivery instrument. Therefore, the profile of the flexible anchor is minimized and substantially conforms with the profile of the delivery instrument. This configuration minimizes trauma to the annulus 22. The free ends 1942, 1946 of the suture 1934 trail behind the delivery instrument as it is pushed through the annulus 22. Once the flexible anchor 1952 is positioned outside of the annular wall 22, the free ends of the tensioning mechanism 1942, 1946 are tensioned. The loop 1954 formed within the hollow member 1936 constricts as the tensioning member 1902 is tensioned, causing the hollow member 1936 to constrict and bunch up as the suture 1934 is pulled back through the wall 22. Because the hollow member 1936 is of greater thickness than the tensioning member 1902, it distributes the inward acting force 1956 on the annulus across a greater surface area, keeping the flexible anchor 1952 from pulling through the annulus 22. The implant 1950 may then be inserted into the nuclear space 24 following along the tensioning member 1902 as described in the embodiments above. Other flexible anchoring structures are contemplated, as would be apparent to one skilled in the art.

Figure 39:
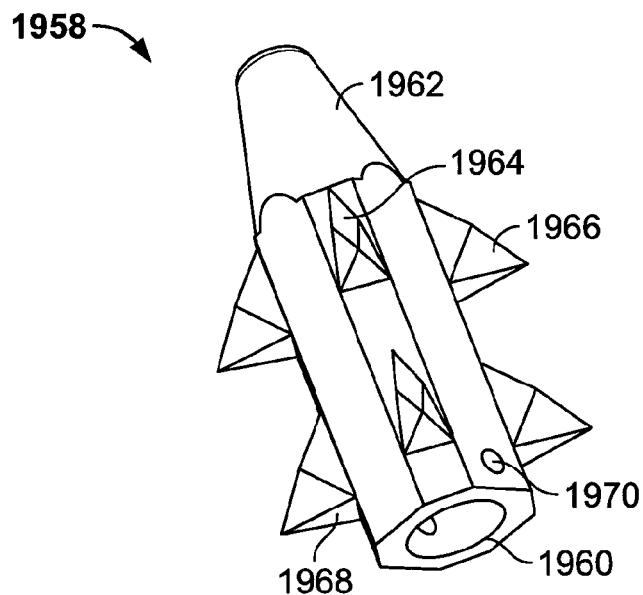
FIG. 39 is a perspective view of a seventh embodiment of an implant retention device in the form of a barbed anchoring device.
Figure 40:
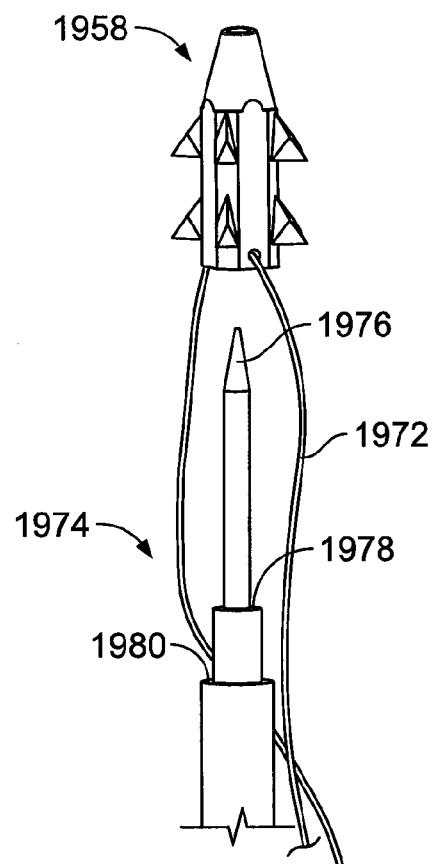
FIG. 40 is a partial perspective view of the anchoring device of FIG. 39 with a third embodiment of the anchoring device insertion tool.
Figure 41:
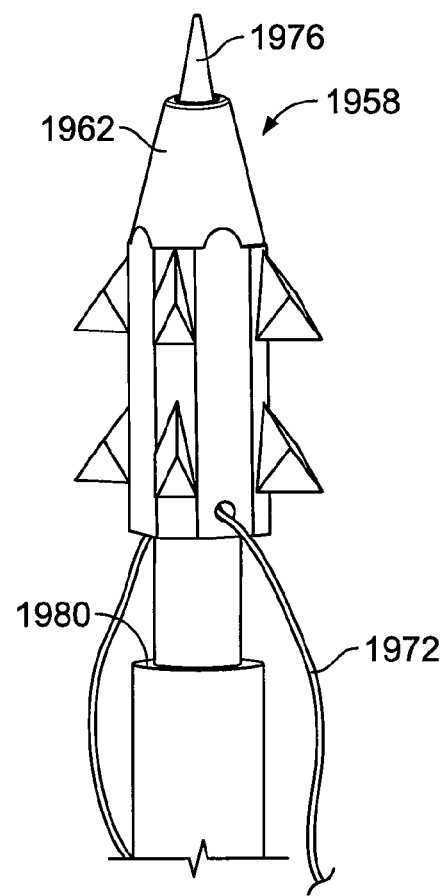
FIG. 41 is an enlarged partial perspective view of the anchoring device and insertion tool of FIGS. 39 and 40.

In another embodiment, the securing mechanism may be embedded within the annular wall 22. In a preferred embodiment, the securing mechanism takes the form of an elongate anchor 1958 with retention structure disposed on the outer surface of the anchor. As shown in FIGS. 39-41, the anchor 1958 has an elongate body with a central throughbore 1960 and one tapered forward end 1962. The outer surface of the anchor has retention structure in the form of protrusions, such as projecting barbs 1964. The barbs 1964 are evenly and radially spaced in four longitudinally disposed rows with two barbs 1964 in each row. Each barb 1964 has a rearwardly sloped front edge 1966 and a rearward face 1968 oriented generally transversely with respect to the longitudinal axis of the anchor 1958. With this configuration, the barbs 1964 allow forward movement through the annulus 22, but resist rearward movement. Other forms of retention structure are envisioned, such has prongs, hooks, teeth, knobs, bumps, or other structure effective to anchor the securing member within the annulus 22. In addition, the anchor body may be formed in any shape effective to be inserted into or through the annular wall 22. Near the rearward end of the anchor 1958 is a tensioning member fastening structure, such as a throughbore 1970 extending transversely to the longitudinal axis through the anchor 1958. The tensioning member 1902, such as a suture 1972, may be threaded through the throughbore 1970 prior to insertion into the annular wall 22.

To insert the anchor 1958, an insertion tool 1974 is provided. In a preferred embodiment shown in FIG. 40, the insertion tool 1974 has a cone-shaped tip 1976 on the distal end to help protrude through the annular wall 22. Proximally spaced from the cone-shaped tip 1976 is a first enlarged shoulder 1978, which provides axial support to the anchor 1958 when it is inserted on the tip 1976 of the instrument. A second enlarged shoulder 1980, radially larger than the first shoulder 1978 is spaced proximally from the first enlarged shoulder 1978 to provide a stop when the tip 1976 is fully inserted into the annular wall 22. The second enlarged shoulder 1980 keeps the anchor 1958 from being inserted through the outer wall 1928 of the annulus 22. After the tensioning member 1902 has been attached to the anchor 1958, the anchor 1958 is then placed on the distal end of the insertion tool 1974. The anchor 1958 is then inserted through the annular window 30 and into the annular wall 22. When the tool 1974 is retracted, the anchor 1958 remains in position within the wall 22 with the tensioning member 1902 extending back into the nuclear space 24 and through the annular window 30. The implant 50 may then be inserted using the tensioning member 1902 as a guide and securely fastened to the tensioning member 1902 as described above.

Figure 42:
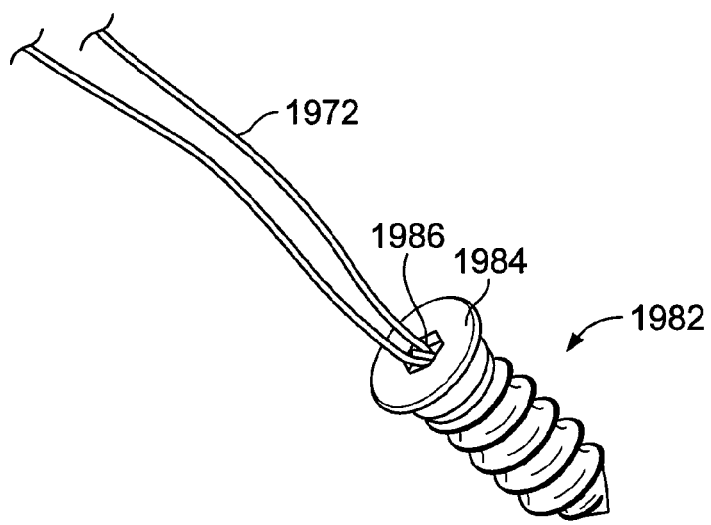
FIG. 42 is a perspective view of an eighth embodiment of an implant retention device in the form of screw-type fastener.

In an alternate embodiment, the anchor may take the form of a screw-like fastener 1982 shown in FIG. 42. This way, the anchor can be rotatably driven into the annular wall 22 instead of being linearly driven directly into the wall 22, as in the previous embodiment. This type of anchor may cause less trauma to the annulus 22 when being inserted or removed from the annular wall 22.

Figure 43:
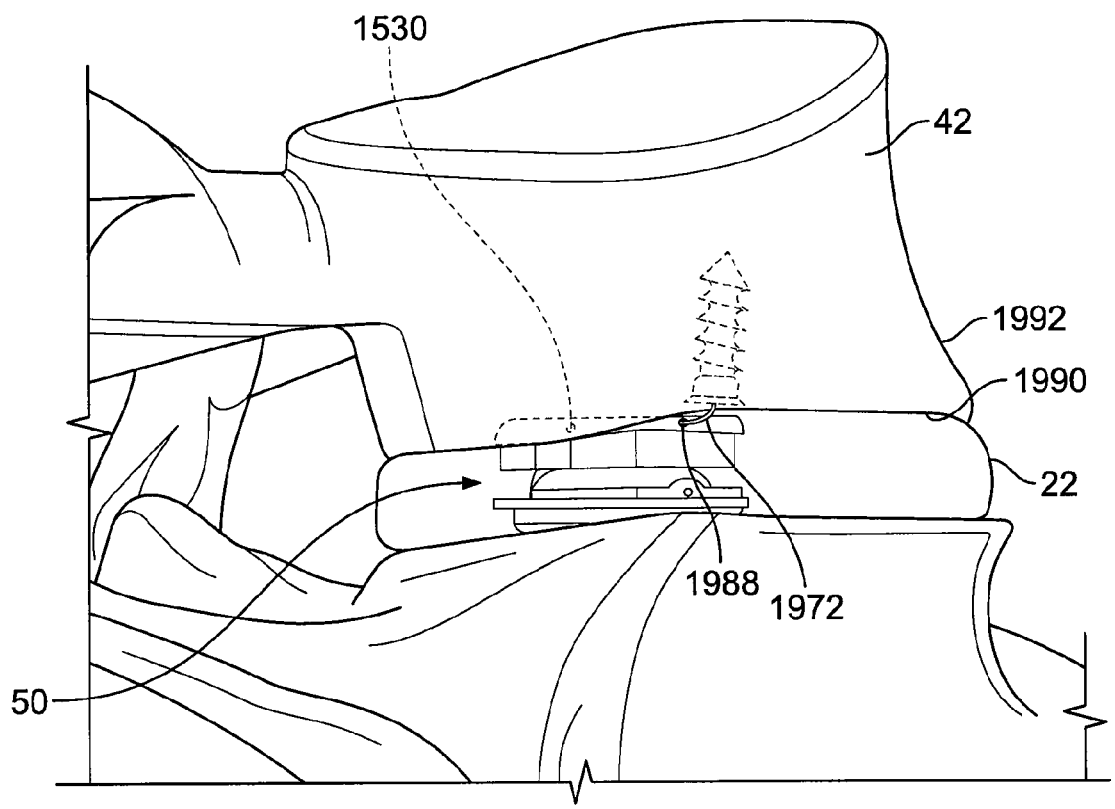
FIG. 43 is a perspective view of the fastener of FIG. 42 coupled to an upper vertebra with the nuclear implant restrained by the tensioning member threaded through the implant and connected to the fastener.

In another embodiment for securing an implant shown in FIGS. 42-43, the securing mechanism may take the form of a fastener secured directly to the vertebra 42 with a tensioning mechanism 1902 tethering the implant 50 to the fastener. In one embodiment, the fastener is a bone screw 1982 having a tensioning mechanism securing portion on the head 1984 of the screw 1982. The securing portion may take the form of a hook or an eye 1986, such that the tensioning mechanism 1902, such as a suture 1972, may be threaded through the eye 1986 so that both free ends of the suture 1972 are free to guide and be fastened to the implant 50. As described above, the tensioning mechanism 1902 may be attached to the implant 50 through a guide portion, such as a channel protruding through a portion of the implant 50. In the embodiment of FIG. 43, the implant has both longitudinal 1530 and lateral channels 1988. The suture 1972 is threaded through the lateral channel 1988 and fastened at the other end of the channel 1988. The screw 1982 may be fastened to the endplate 1990, or alternatively to an outer face 1992 of one of the adjacent vertebrae 42.

In all of the above-mentioned embodiments, the tensioning member may alternatively be provided as a bioresorbable suture. In some cases, after a certain period of time after the implant has been implanted within the intervertebral space, the implant will subside into the tissue which contacts the weight bearing surfaces of the implant. Once this subsidence has taken place, the implant is less likely to be expelled from the nuclear space, and the securing mechanism will no longer be needed. Thus, an absorbable suture is advantageously absorbed by the body after the possibility of expulsion is reduced.

The implant retention devices and features as described herein may be adapted for use with a variety of artificial joint arrangements other than nuclear implants. In addition, the implant retention devices and features as described herein may be adapted for use with a variety of surgical approaches. Most of the surgical approaches shown in the illustrations are from an anterior or lateral approach but are easily adaptable for a posterior approach, for example. In a posterior approach, an incision portal is made in the posterior annulus.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. An implant retention system comprising:
   a weight-bearing nuclear implant including opposite upper and lower outer facing surfaces sized and configured to engage with inner facing surfaces of adjacent upper and lower vertebral bodies to provide load bearing support to the adjacent vertebral bodies within an annulus of an intervertebral disc;
   a shaft having opposite ends with one of the opposite ends connected to and terminating within the implant;
   an annulus anchoring device having a body including a cutting portion configured for cutting through an annular wall of the annulus; and
   an adjustable connection between the anchoring device and the other one of the opposite ends of the shaft to allow the annulus anchoring device to pivot with respect to the shaft between a cutting orientation with the cutting portion leading the annular anchoring device as the shaft and implant connected thereto are advanced together into the annulus to cut into and through the annulus and an anchoring orientation with a non-cutting portion of the annulus anchoring device body oriented to abut against the annular wall to facilitate secure engagement of the annulus anchoring device thereto for keeping the implant in the annulus.

2. The implant retention system of claim 1, wherein the annulus anchoring device body comprises an elongate bar and the adjustable connection includes a recessed portion of the elongate bar for connecting to the other one of the opposite ends of the shaft.

3. The implant retention system of claim 1 wherein the annulus anchoring device body includes a generally triangular barb.

4. The implant retention system of claim 1, wherein the non-cutting portion of the annulus anchoring device body has substantially blunt edges.

5. The implant retention system of claim 1 wherein the implant includes an elongated recess and the one of the opposite ends of the shaft is snap fit into the elongated recess.

6. The implant retention system of claim 5 wherein the other one of the opposite ends of the shaft includes a pair of prongs and the annulus anchoring device body is pivotally disposed between the prongs.

7. The implant retention system of claim 1 wherein the implant further comprises upper and lower members with the upper member including the upper outer facing surface and the lower member including the lower outer facing surface and the upper and lower members are configured to articulate with respect to one another and the one of the opposite ends of the shaft is connected to the upper implant member.

8. The implant retention system of claim 1 wherein the implant comprises upper and lower members with the upper member including the upper outer facing surface and the lower member including the lower outer facing surface and the upper and lower members are configured to articulate with respect to one another and the one of the opposite ends of the shaft is connected to the lower implant member.

9. The implant retention system of claim 1 wherein the adjustable connection allows the annulus anchoring device body to pivot between the cutting orientation wherein a longitudinal axis of the annulus anchoring device body is generally coaxial with or parallel to a longitudinal axis of the shaft and the anchoring orientation wherein the longitudinal axis of the annulus anchoring device body is transverse to the longitudinal axis of the shaft.

10. The implant retention system of claim 1, wherein the implant comprises an elongate body with narrow ends opposite elongated sides thereof and a shaft receiving portion for receiving the one of the opposite ends of the shaft.

11. The implant retention system of claim 10, wherein the shaft receiving portion is disposed at one of the narrow ends.

12. The implant retention system of claim 10, further comprising an adjustable connection between the one of the opposite ends of the shaft and the shaft receiving portion for allowing independent movement of the implant and decreasing corresponding movement of the annulus anchoring device for reducing potential trauma to the annular wall.

13. The implant retention system of claim 1, wherein the nuclear implant has a narrow leading end configured for minimally invasive insertion into a nuclear space within the annulus and the one of the opposite ends of the shaft is connected to the narrow leading end.

14. A method for restraining a nuclear implant, the method comprising:
    positioning an anchoring device such that a longitudinal axis of the anchoring device is generally parallel to or coaxial with the longitudinal axis of a shaft that extends between and is connected at opposite ends thereof to the nuclear implant and the anchoring device with the shaft end connected to the nuclear implant terminating therein;
    sequentially advancing the anchoring device, the shaft, and the connected nuclear implant through an opening in an annular wall of an annulus;
    penetrating through at least a portion of the annular wall generally opposite the opening thereof with a leading sharp cutting edge of the anchoring device with the annular wall extending about the nuclear implant;
    retracting the anchoring device to reorient the anchoring device such that the longitudinal axis of the anchoring device is transverse to the longitudinal axis of the shaft; and
    securing the anchoring device to the annular wall such that the nuclear implant is anchored solely to the annular wall by the anchoring device to restrain movement of the implant to retain the implant within the annulus with the annular wall extending thereabout and the implant in load bearing engagement with the adjacent vertebrae.

15. The method of claim 14 further comprising fastening the shaft to a leading end of the implant.

16. The method of claim 14, further comprising penetrating an outer surface of the annular wall with at least a portion of the anchoring device.

17. The method of claim 14, further comprising connecting the shaft to a leading end of the nuclear implant prior to insertion into the annulus.

18. The method of claim 14, further comprising positioning the nuclear implant within the annulus between the anchoring device and the annular wall opening.

* * * * *